United States Patent [19]

Honda et al.

[11] Patent Number: 4,774,342

[45] Date of Patent: Sep. 27, 1988

[54] NOVEL AILANTHONE DERIVATIVE

[75] Inventors: Tadashi Honda, Ibaraki; Toshio Tatsuoka, Osaka; Toshihiro Nakanishi, Ibaraki, all of Japan

[73] Assignee: Suntory Limited, Osaka, Japan

[21] Appl. No.: 794,331

[22] Filed: Nov. 4, 1985

Related U.S. Application Data

[63] Continuation of Ser. No. 548,573, Nov. 4, 1983, abandoned.

[30] Foreign Application Priority Data

Nov. 8, 1982 [JP] Japan ................. 57-196248
Sep. 29, 1983 [JP] Japan ................. 58-179279

[51] Int. Cl.$^4$ ........................................ C07D 493/08
[52] U.S. Cl. ............................................. 549/275
[58] Field of Search ......................................... 549/275

[56] References Cited

U.S. PATENT DOCUMENTS 3,969,369  7/1976  Kupchan et al. ............... 549/275

FOREIGN PATENT DOCUMENTS 0080570  6/1983  European Pat. Off. ........... 549/275
1440094  6/1976  United Kingdom .

OTHER PUBLICATIONS

Johnson et al., Cancer Treatment Reviews, 1975, 2, 1–31.
Pratt et al., The Anticancer Drugs, Oxford Univ. Press, N.Y., 1979, pp. 273–277.
Cassady et al., Anticancer Agents Based on Natural Product Models, 1980, pp. 255–269.
Kupchan et al., J. Org. Chem., vol. 40, No. 5, 1975, p. 645 and p. 654.

*Primary Examiner*—Jane T. Fan
*Attorney, Agent, or Firm*—Burns, Doane, Swecker & Mathis

[57] ABSTRACT

An ailanthone derivative having the general formula:

wherein R is a p-alkyl benzoic acid residue having 8 to 21 carbon atoms, a 2-methyl saturated fatty acid residue having 6 to 19 carbon atoms, a 2-methyl-2-unsaturated fatty acid residue having 4 to 19 carbon atoms, a 3,4-dimethyl-4-acyloxy-2-pentenoic acid residue having 9 to 19 carbon atoms, a 3,4,4-trimethyl-2-unsaturated fatty acid residue having 8 to 21 carbon atoms, a group having the formula wherein n is an integer of 1 to 13, a group having the general formula wherein n is an integer of 1 to 13, a trans-cinnamic acid residue, a linear saturated fatty acid residue having 3 to 22 carbon atoms, a 3-methyl-2-unsaturated fatty acid residue having 6 to 19 carbon atoms, a 3,4-dimethyl-2-unsaturated fatty acid residue having 7 to 20 carbon atoms, a terpenic acid residue, a 2-amino saturated fatty acid residue having 2 to 18 carbon atoms or a salt thereof, a 2-hydroxy saturated fatty acid residue having 3 to 18 carbon atoms, or a 3,5,5-trimethylhexanoic acid residue.

5 Claims, No Drawings

NOVEL AILANTHONE DERIVATIVE

This application is a continuation of application Ser. No. 548,573, filed Nov. 4, 1983, now abandoned.

BACKGROUND OF THE INVENTION

1. Field of the Invention

The present invention relates to a novel ailanthone derivative having an antineoplastic activity.

2. Description of the Prior Art

Various attempts have been heretofore made to evaluate antineoplastic or antitumor effects of natural substances and compounds derived from natural substances. Of these substances and compounds, some have been clinically used as an antineoplastic or antitumor agent. However, these agents are still insufficient for clinical use in view of either their effects or toxicity. That is, the effective agents generally have the disadvantage of toxicity, while less toxic agents are less effective.

Of these natural substances, it is known that bruceantin having the general formula (2):

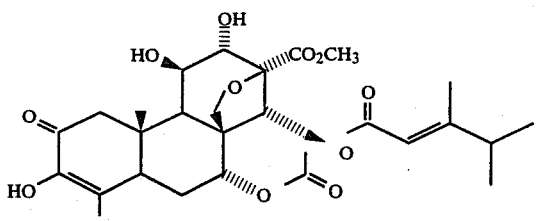

is included in *Brucea antidysenterica* Mill belonging to Simarubaceae, which has been used for curing cancer in Ethiopia, as disclosed in Kupchans et al, J. Org. Chem., 38, 178 (1973), J. Org. Chem., 40, 648 (1975), U.S. Pat. No. 3,969,369, and British Pat. No. 144094. Then, various quassinoid compounds such as bruceoside A, dehydroailanthinone, glaucarubinone have been synthesized and the antitumor effects thereof have been evaluated as disclosed in J. Org. Chem., 40, 654 (1975), ibid 44, 2180 (1979), J. Pharm. Sci., 68, 883 (1979), and Cancer Treatment Reports, 60, 1031 (1976). However, these quassinoid compounds are still not sufficient from the viewpoints of their effectiveness and toxicity.

SUMMARY OF THE INVENTION

Accordingly, the objects of the present invention are to improve the above-mentioned state of the prior art and to provide novel ailanthone derivatives having a remarkable antineoplastic activity.

Other objects and advantages of the present invention will be apparent from the following description.

In accordance with the present invention, there is provided an ailanthone derivative having the general formula:

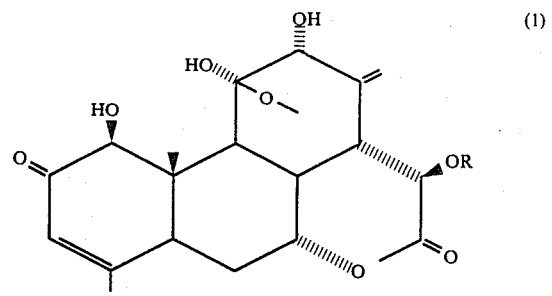

wherein R is a p-alkyl benzoic acid residue having 8 to 21 carbon atoms, a 2-methyl saturated fatty acid residue having 6 to 19 carbon atoms, a 2-methyl-2-unsaturated fatty acid residue having 4 to 19 carbon atoms, a 3,4-dimethyl-4-acyloxy-2-pentenoic acid residue having 9 to 19 carbon atoms, a 3,4,4-trimethyl-2-unsaturated fatty acid residue having 8 to 21 carbon atoms, a group having the formula

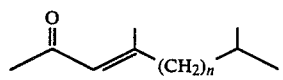

wherein n is an integer of 1 to 13, a group having the general formula

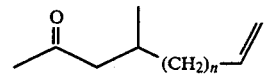

wherein n is an integer of 1 to 13, a trans-cinnamic acid residue, a linear saturated fatty acid residue having 3 to 22 carbon atoms, a 3-methyl-2-unsaturated fatty acid residue having 6 to 19 carbon atoms, a 3,4-dimethyl-2-unsaturated fatty acid residue having 7 to 20 carbon atoms, a terpenic acid residue, a 2-amino saturated fatty acid residue having 2 to 18 carbon atoms or a salt thereof, a 2-hydroxy saturated fatty acid residue having 3 to 18 carbon atoms, or a 3,5,5-trimethylhexanoic acid residue. The term "terpenic acid residue" herein means the residues of geranic acid, neric acid, farnesic acid, and retinoic acid (i.e., vitamin $A_1$).

DESCRIPTION OF THE PREFERRED EMBODIMENT

The present inventors have heretofore noticed ailanthone (i.e., $11\beta$, 20-epoxy-$1\beta$, $11\alpha$, $12\alpha$-trihydroxypicrasa-3,13(21)-diene-2,16-dione) having the following formula (3):

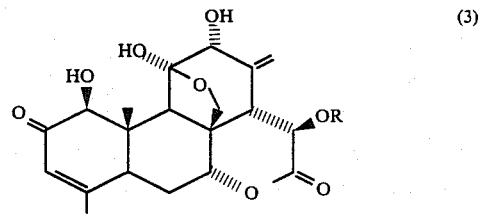

This triterpene compound is contained in *Ailanthus altissima*, swingle, Simaroubaceae. In the course of the study, various derivatives of ailanthone are synthesized and subjected to antineoplastic screening tests. As a result, the above-mentioned ailanthone derivatives having the general formula (1) having a remarkable antineoplastic activity have been found.

The novel ailanthone derivatives having the general formula (1) according to the present invention can be prepared, for example, from ailanthone (3) as follows:

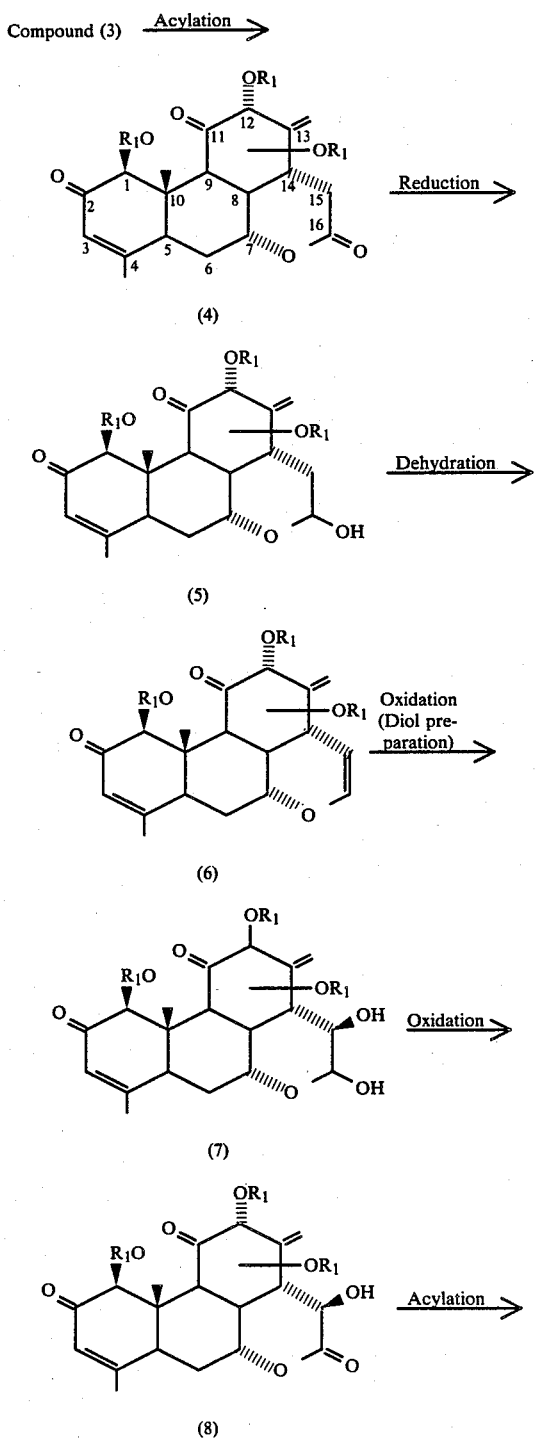

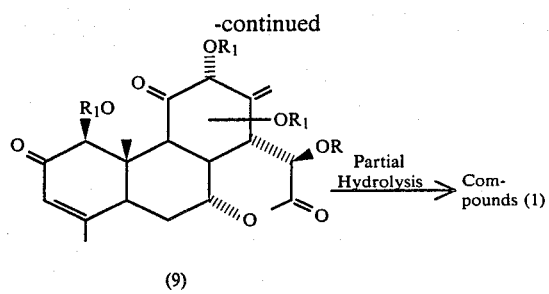

wherein $R_1$ is an acyl group such as an acetyl group, a chloroacetyl group, or a benzoyl group and R is a p-alkyl benzoic acid residue having 8 to 21 carbon atoms, a 2-methyl saturated fatty acid residue having 6 to 19 carbon atoms, a 2-methyl-2-unsaturated fatty acid residue having 4 to 19 carbon atoms, a 3,4,4-trimethyl-2-unsaturated fatty acid residue having 8 to 21 carbon atoms, a group having the formula

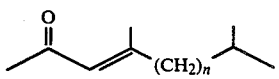

wherein n is an integer of 1 to 13, a group having the general formula

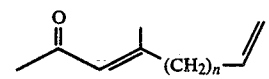

wherein n is an integer of 1 to 13, a trans-cinnamic acid residue, a linear saturated fatty acid residue having 3 to 22 carbon atoms, a 3-methyl-2-unsaturated fatty acid residue having 6 to 19 carbon atoms, a 3,4-dimethyl-2-unsaturated fatty acid residue having 7 to 20 carbon atoms, a terpenic acid residue.

That is, ailantone (3) extracted and isolated from *Ailanthus altissima* swingle, Simaroubaceae in a conventional manner is first acylated by using an acylating agent such as acetic anhydride, acetyl chloride, benzoyl chloride, or chloroacetyl chloride to form a 1,12,20-triacyl compound (4). This reaction is carried out to substantially protect the free hydroxyl groups from reaction reagents in the ailanthone (3) during the subsequent reduction, dehydration, and oxidation steps. Accordingly, any acylating agent can be used in the acylation step. During the course of the acylation, the hemiacetal group at the 11-position is cleaved whereby the 20-position is acylated.

Then, the triacyl compound (4) of which 1, 12, and 20-positions are protected by acyl groups is selectively reduced by using a selective reduction agent such as sodium borohydride or lithium borohydride to convert the compound (4) into the secondary alcohol compound (5) by the selective reduction of the ketone group at the 16-position. The resultant compound (5) is naturally a mixture of the stereoisomers. The compound (5) thus obtained is, then, treated with a dehydrating agent such as phosphoryl chloride or phosphorus pentoxide to form the corresponding compound (6) having a double bond between the 15- and 16-positions. The compound (6) is oxidized by, for example, a combination of N-methylmorpholine-N-oxide and osmium tetroxide or osmium tetroxide alone to form the corresponding 15,16-dihydroxy compounds (7).

The 15,16-dihydroxy compound (7) is, then, moderately oxidized by using a mild oxidizing agent such as silver oxide to form the 16-ketone compound (8). The 16-ketone compound (8) is acylated by p-alkyl benzoic acid, 2-methyl saturated fatty acid, 2-methyl-2-unsaturated fatty acid, 3,4,4-trimethyl-2-unsaturated fatty acid, a compound having the formula:

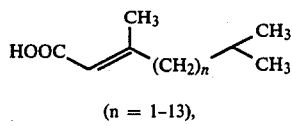

(n = 1-13), a compound having the formula:

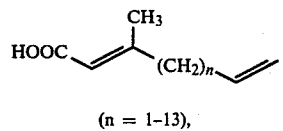

(n = 1-13), trans-cinnamic acid, a linear saturated fatty acid, 3-methyl-2-saturated fatty acid, 3,4-dimethyl-2-unsaturated fatty acid, terpenic acid, or 3,5,5-trimethylhexanoic acid to form the ailanthone derivative (9). This acylation can be achieved by the following method:

Above acylation can be achieved by the following methods (i) the acid chloride or acid anhydride of the above-mentioned carboxylic acid and a weak base (e.g., triethylamine or pyridine) or a base (e.g., potassium carbonate or sodium carbonate) or (ii) the above-mentioned carboxylic acid and 1-ethyl-2-fluoropyridinium tetrafluoroborate; 1-methyl-2-fluoropyridinium tosylate; 1-methyl-2-chloropyridinium tosylate and cesium fluoride; or 4-dimethylaminopyridine.

The ailanthone derivative (9) is hydrolyzed under a relatively mild hydrolyzing condition to form the desired ailanthone derivative (1). When the hydrolysis of the compound (9) is carried out under too strong a hydrolyzing condition, the ester group at the 15-position is undesirably hydrolyzed. Thus, severe hydrolysis should be avoided. Mild hydrolysis can be carried out by effecting the reaction in, for example, a dilute alcoholic solution of alkali metal alkoxide or an alcohol solution of alkali metal alkoxide and an equivalent amount of 18-crown-6.

In the case of R being a 2-hydroxy saturated fatty acid residue having 3 to 18 carbon atoms in the general formula (1), the desired ailanthone derivatives can be prepared from the above-mentioned compound (8) as follows:

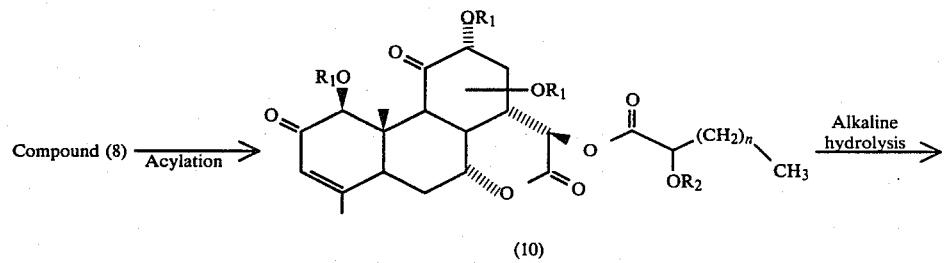

(10)

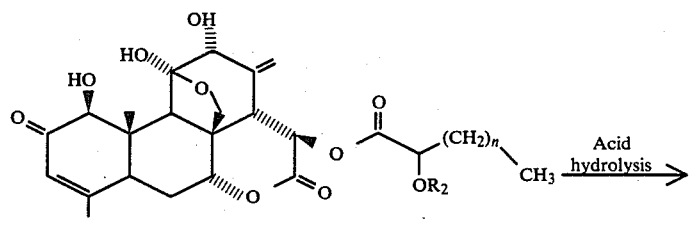

(11)

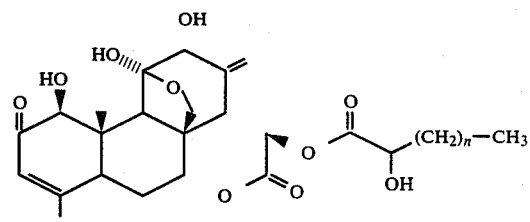

(1)

wherein $R_1$ is the same as defined above, $R_2$ is a protective group such as methoxy methyl group or methoxyethoxy methyl group, and n is an integer of 0 to 15.

That is, the ketone compound (8) is reacted with 2-methoxymethyloxy carboxylic acid in any of the esterification methods mentioned above. The 2-methoxymethyloxy carboxylic acid can be prepared according to any conventional manner. Thus, the compound (10) is obtained. Then, the compound (10) is deacylated under the above-mentioned hydrolysis condition to form the compound (11). The compound (11) is then acid hydrolyzed in, for example, a methanol solution saturated with dry hydrogen chloride to form the desired ailanthone derivative (1).

Also, in the case of a 3,4-dimethyl-4-acyloxy-2-pentenoic acid residue being present at the 15-position in the general formula (1), the desired ailanthone derivatives can be prepared from the above-mentioned compound (8) as follows:

acid, 1-ethyl-2-fluoropyridinium tetrafluoroborate or 1-methyl-2-fluoropyridinium tosylate or 1-methyl-2-chloropyridinium tosylate, cesium fluoride, and 4-dimethylaminopyridine. Thus, the compound (12) can be obtained. The compound (12) is reacted with, for example, zinc bromide in methylene chloride to form the compound (13). The compound (13) thus obtained is acylated with, for example, the acid anhydride of a linear saturated fatty acid having 2 to 12 carbon atoms, triethylamine, or 4-dimethylaminopyridine to form the compound (14). The compound (14) thus acylated is selectively deacylated under the above mentioned hydrolysis condition to form the compound (1). Thus, the

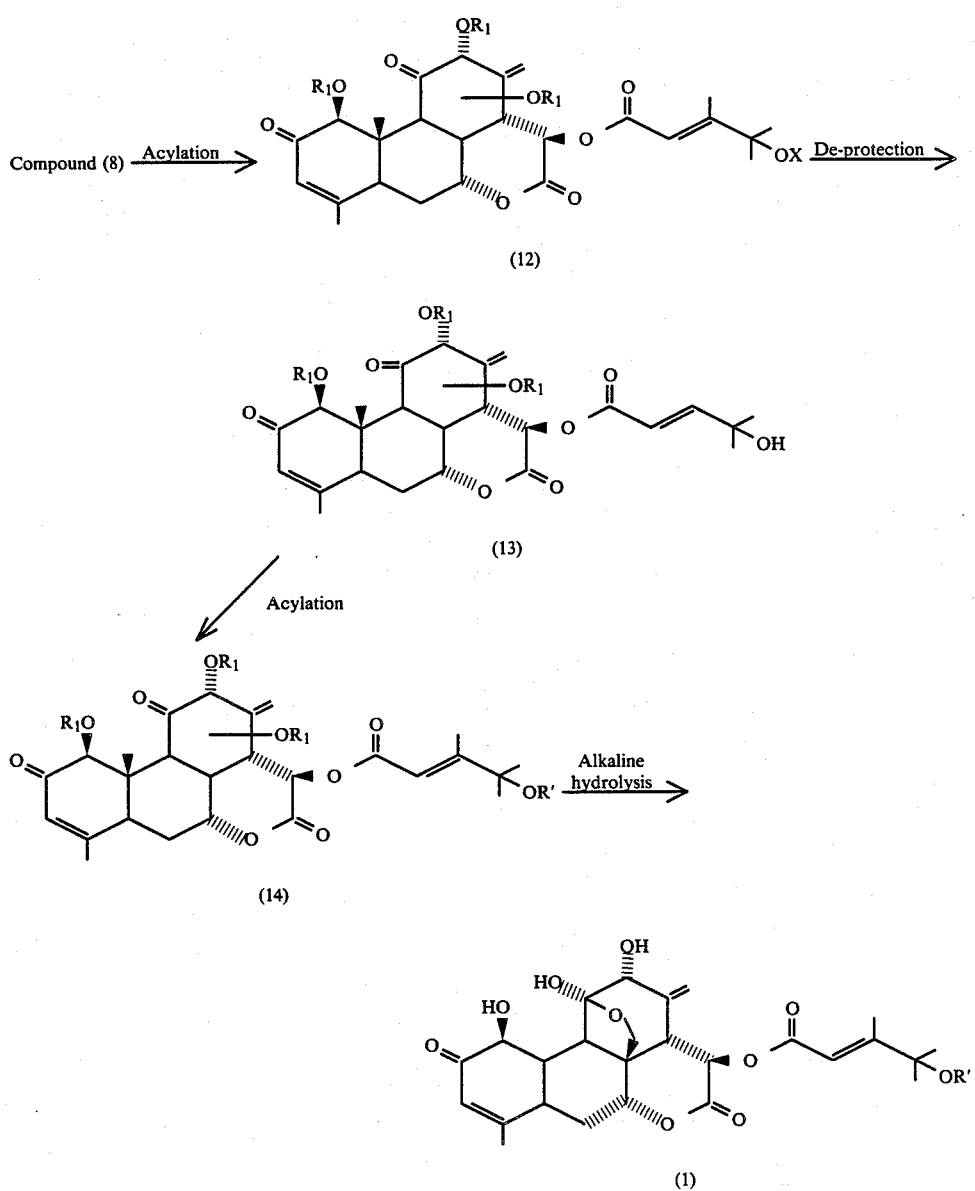

wherein R₁ is the same as defined above, R' is a linear saturated fatty acid residue having 2 to 12 carbon atoms, and X is a protective group.

That is, the ketone compound (8) is acylated with 3,4-dimethyl-4-methoxyethoxymethyloxy-2-pentenoic desired ailanthone derivative (1) can be obtained.

Furthermore, in the case of a 2-amino acid residue or its salt being present at the 15-position, the desired ailanthone compound can be prepared from the above-mentioned compound (8) as follows:

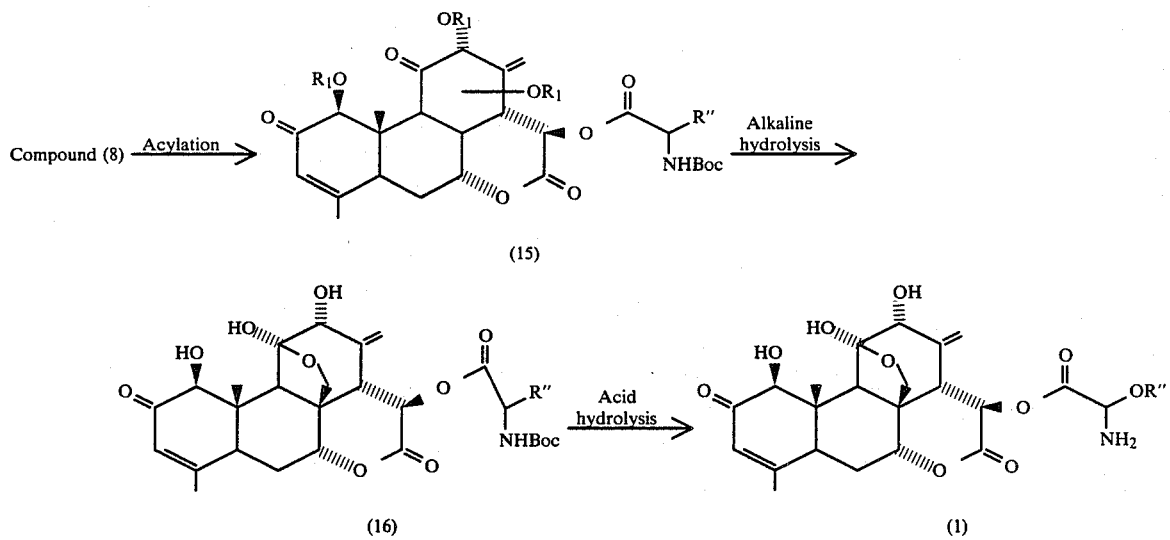

(15)

(16)    (1)

wherein R₁ is the same as defined above, Boc is a t-butoxy carbonyl group, R" is a 0 to 16 carbon chain.

That is, the ketone compound (8) is reacted with 2-(N-t-butoxycarbonyl) amino carboxylic acid according to any esterification method mentioned above. The 2-(N-t-butoxycarbonyl) amino carboxylic acid can be prepared in a manner as described in Tetrahedron Letters, 4393 (1975). Thus, the compound (15) is formed. The compound (15) thus formed is deacylated under the above-mentioned hydrolysis condition to give the compound (16). The compound (16) can be hydrolyzed in, for example, an ethyl acetate solution saturated with hydrogen chloride to form the compound (1).

Examples of the substituents R in the present ailanthone derivatives (1) are p-alkyl benzoic acid residues having 8 to 21 carbon atoms such as p-methyl benzoic acid residue, p-ethyl benzoic acid residue, p-propyl benzoic acid residue, p-butyl benzoic acid residue, p-pentyl benzoic acid residue, p-hexyl benzoic acid residue, p-heptyl benzoic acid residue, p-octyl benzoic acid residue, p-nonyl benzoic acid residue, p-decyl benzoic acid residue, p-undecyl benzoic acid residue, p-dodecyl benzoic acid residue, p-tridecyl benzoic acid residue, and p-tetradecyl benzoic acid residue; 2-methyl-2-unsaturated fatty acid residues having 4 to 19 carbon atoms such as 2-methyl-2-propenoic acid residue, 2-methyl-2-butenoic acid (i.e., tiglic acid) residue, 2-methyl-2-pentenoic acid residue, 2-methyl-2-hexenoic acid residue, 2-methyl-2-heptenoic acid residue, 2-methyl-2-octenoic acid residue, 2-methyl-2-nonenoic acid residue, 2-methyl-2-decenoic acid residue, 2-methyl-2-undecenoic acid residue, 2-methyl-2-dodecenoic acid residue, 2-methyl-2-tridecenoic acid residue, 2-methyl-2-tetradecenoic acid residue, 2-methyl-2-pentadecenoic acid residue, 2-methyl-2-hexadecenoic acid residue, 2-methyl-2-heptadecenoic acid residue, and 2-methyl-2-octadecenoic acid residue; 2-methyl saturated fatty acid residues having 6 to 19 Carbon atoms such as 2-methylpentanoic acid residue, 2-methylhexanoic acid residue, 2-methylheptanoic acid residue, 2-methyloctanoic acid residue, 2-methylnonanoic acid residue, 2-methyldecanoic acid residue, 2-methylundecanoic acid residue, 2-methyldodecanoic acid residue, 2-methyltridecanoic acid residue, 2-methyltetradecanoic acid residue, 2-methylpentadecanoic acid residue, 2-methylhexadecanoic acid residue, 2-methylheptadecanoic acid residue, 2-methyloctadecanoic acid residue; 3,4-dimethyl-4-acyloxy-2-pentenoic acid residues having 9 to 19 carbon atoms such as, 3,4-dimethyl-4-acetoxy-2-pentenoic acid residue, 3,4-dimethyl-4-propionyloxy-2-pentenoic acid residue, 3,4-dimethyl-4-butanoyloxy-2-pentenoic acid residue, 3,4-dimethyl-4-pentanoyloxy-2-pentenoic acid residue, 3,4-dimethyl-4-hexanoyloxy-2-pentenoic acid residue, 3,4-dimethyl-4-octanoyloxy-2-pentenoic acid residue, 3,4-dimethyl-4-nonanoyloxy-2-pentenoic acid residue, 3,4-dimethyl-4-decanoyloxy-2-pentenoic acid residue, 3,4-dimethyl-4-undecanoyloxy-2-pentenoic acid residue, and 3,4-dimethyl-4-dodecanoyloxy-2-pentenoic acid residue; 3,4,4-trimethyl-2-unsaturated fatty acid residues having 8 to 21 carbon atoms such as 3,4,4-trimethyl-2-pentenoic acid residue, 3,4,4-trimethyl-2-hexenoic acid residue, 3,4,4-trimethyl-2-heptenoic acid residue, 3,4,4-trimethyl-2-octenoic acid residue, 3,4,4-trimethyl-2-nonenoic acid residue, 3,4,4-trimethyl-2-decenoic acid residue, 3,4,4-trimethyl-2-undecenoic acid residue, 3,4,4-trimethyl-2-dodecenoic acid residue, 3,4,4-trimethyl-2-trideceonic acid residue, 3,4,4-trimethyl-2-tetradecenoic acid residue, 3,4,4-trimethyl-2-pentadecenoic acid residue, 3,4,4-trimethyl-2-hexadecenoic acid residue, 3,4,4-trimethyl-2-heptadecenoic acid residue, and 3,4,4-trimethyl-2-octadecenoic acid residue; groups having the formula:

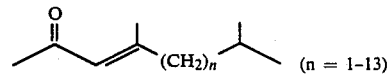

(n = 1-13)

such as 3,5-dimethyl-2-hexenoic acid residue, 3,6-dimethyl-2-heptenoic acid residue, 3,7-dimethyl-2-octenoic acid residue, 3,8-dimethyl-2-nonenoic acid residue, 3,9-dimethyl-2-decenoic acid residue, 3,10-dimethyl-2-undecenoic acid residue, 3,11-dimethyl-2- dodecenoic acid residue, 3,12-dimethyl-2-tridecenoic acid residue, 3,13,-dimethyl-2-tetradecenoic acid residue, 3,14-dimethyl-2-pentadecenoic acid residue, 3,15-dimethyl-2-hexadecenoic acid residue, 3,16-dimethyl-2-heptadecenoic acid residue, and 3,17-dimethyl-2-octadecenoic acid residue; groups having the formula:

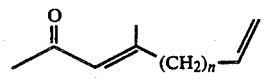

(n = 1–13)

such as 3-methyl-2,5-hexadienoic acid residue, 3-methyl-2,6-heptadienoic acid residue, 3-methyl-2,7-octadienoic acid residue, 3-methyl-2,8-nonadienoic acid residue, 3-methyl-2,9-decadienoic acid residue, 3-methyl-2,10-undecadienoic acid residue, 3-methyl-2,11-dodecadienoic acid residue, 3-methyl-2,12-tridecadienoic acid residue, 3-methyl-2,13-tetradecadienoic acid residue, 3-methyl-2,14-pentadecadienoic acid residue, 3-methyl-2,15-hexadecadienoic acid residue, 3-methyl-2,16-heptadecadienoic acid residue, and 3-methyl-2,17-octadecadienoic acid residue; trans-cinnamic acid residue; linear saturated fatty acid residues having 3 to 22 carbon atoms such as propanoic acid residue, butanoic acid residue, pentanoic acid residue, hexanoic acid residue, heptanoic acid residue, octanoic acid residue, nonanoic acid residue, decanoic acid residue, undecanoic acid residue, dodecanoic acid residue, tridecanoic acid residue, tetradecanoic acid residue, pentadecanoic acid residue, hexadecanoic acid residue, heptadecanoic acid residue, octadecanoic acid residue, nonadecanoic acid residue, eicosanoic acid residue, heneicosanoic acid residue, decosanoic acid residue, and 3,5,5-trimethylhexanoic acid residue; 3-methyl-2-unsaturated fatty acid residues having 6 to 19 carbon atoms such as 3-methyl-2-pentenoic acid residue; 3-methyl-2-hexenoic acid residue, 3-methyl-2-heptenoic acid residue 3-methyl-2-octenoic acid residue, 3-methyl-2-nonenoic acid residue, 3-methyl-2-decenoic acid residue, 3-methyl-2-undecenoic acid residue, 3-methyl-2-tridecenoic acid residue, 3-methyl-2-tetradecenoic acid residue, 3-methyl-2-pentadecenoic acid residue, 3-methyl-2-hexadecenoic acid residue, 3-methyl-2-heptadecenoic acid residue, and 3-methyl-2-octadecenoic acid residue; 3,4-dimethyl-2-unsaturated fatty acid residues having 7 to 20 carbon atoms such as 3,4-dimethyl-2-pentenoic acid residue, 3,4-dimethyl-2-hexenoic acid residue, 3,4-dimethyl-2-heptenoic acid residue, 3,4-dimethyl-2-octenoic acid residue, 3,4-dimethyl-2-nonenoic acid residue, 3,4-dimethyl-2-decenoic acid residue, 3,4-dimethyl-2-undecenoic acid residue, 3,4-dimethyl-2-dodecenoic acid residue, 3,4-dimethyl-2-tridecenoic acid residue, 3,4-dimethyl-2-tetradecenoic acid residue, 3,4-dimethyl-2-pentadecenoic acid residue, 3,4-dimethyl-2-hexadecenoic acid residue, 3,4-dimethyl-2-heptadecenoic acid residue, and 3,4-dimethyl-2-octadecenoic acid residue; terpenic acid residues such as geranic acid residue (i.e., 3,7-dimethyl-2(trans), 6-octadienoic acid residue), neric acid residue (i.e., 3,7-dimethyl-2(cis), 6-octadienoic acid residue), trans-trans-farnesic acid residue (i.e., 3,7,11-trimethyl-2(trans), 6(trans), 10-dodecatrienoic acid residue), cis-trans-farnesic acid residue (i.e., 3,7,11-trimethyl-2(cis), 6(trans), 10-dodecatrienoic acid residue), and vitamin $A_1$ acid residue (i.e., retinoic acid residue); 2-amino saturated fatty acid residues having 2 to 18 carbon atoms or their salts such as L-leucine residue, D-leucine residue, L-alanine residue, D-alanine residue, L-2-aminobutanoic acid residue, D-2-aminobutanoic acid residue, L-2-aminopentanoic acid residue, D-2-aminopentanoic residue, L-2-aminohexanoic acid residue, D-2-aminohexanoic acid residue, L-2-aminoheptanoic acid residue, D-2-aminoheptanoic acid residue, L-2-aminooctanoic acid residue, D-2-aminooctanoic acid residue, L-2-aminononanoic acid residue, D-aminononanoic acid residue, L-2-aminodecanoic acid residue, D-2-aminodecanoic acid residue, L-2-aminoundecanoic acid residue, D-2-aminoundecanoic acid residue, L-2-aminododecanoic acid residue, D-2-aminododecanoic acid residue, L-2-aminotridecanoic acid residue, D-2-aminotridecanoic acid residue, L-2-aminotetradecanoic acid residue, D-2-aminotetradecanoic acid residue, L-2-aminopentadecanoic acid residue, D-2-aminopentadecanoic acid residue, L-2-aminohexadecanoic acid residue, D-2-aminohexadecanoic acid residue, L-2-aminoheptadecanoic acid residue, D-2-aminoheptadecanoic acid residue, L-2-aminooctadecanoic acid residue, D-2-aminooctadecanoic acid residue, and the salts thereof (e.g., hydrogenchloride, hydrogen-bromide trifluoroaceticacid; 2-hydroxy saturated fatty acid residues having 3 to 18 carbon atoms such as 2-hydroxypropanoic acid residue, 2-hydroxybutanoic acid residue, 2-hydroxypentanoic acid residue, 2-hydroxyhexanoic acid residue, 2-hydroxyheptanoic acid residue, 2-hydroxyoctanoic acid residue, 2-hydroxynonanoic acid residue, 2-hydroxydecanoic acid residue, 2-hydroxyundecanoic acid residue, 2-hydroxydodecanoic acid residue, 2-hydroxytridecanoic acid residue, 2-hydroxytetradecanoic acid residue, 2-hydroxypentadecanoic acid residue, 2-hydroxyhexadecanoic acid residue, 2-hydroxyheptadecanoic acid residue, and 2-hydroxyoctadecanoic acid residue; and 3,5,5-trimethylhexanoic acid residue.

EXAMPLES

The present invention now will be further illustrated by, but is by no means limited to, the following examples. The 15β-hydroxyailanthone triacetates (i.e., the above-mentioned compound (8): $R_1$=COCH$_3$) used as a starting material in Examples 1 to 4 were prepared in the same manner as disclosed in Examples 1 to 5, respectively, of U.S. patent application Ser. No. 421,200 filed on Sept. 22, 1982.

EXAMPLE 1

Synthesis No. 1 of Triacetyl Compound (9) ($R_1$=COCH$_3$) (i.e., 15β-hydroxyailanthone triacetate-carboxylic acid esters)

A carboxylic acid (1.24 equivalent) and 1-ethyl-2-fluoropyridinium tetrafluoroborate or 1-methyl-2-fluoropyridinium tosylate or 1-methyl-2-chloropyridinium tosylate (1.50 equivalent) were dissolved in anhydrous methylene chloride and, then, cesium fluoride (4.87 equivalent) was added thereto. The resultant solution was stirred at room temperature for 30 minutes and, then, 1.00 g (1.98 mM) of 15β-hydroxyailanthone triacetate (i.e., the compound (8): $R_1$=COCH$_3$) was added, all at once, to the solution under a nitrogen atmosphere.

The solution was allowed to stand at room temperature for 20 hours while stirring. Thus, the reaction was completed.

The reaction mixture thus obtained was extracted three times with methylene chloride. The solvent phase thus obtained was washed twice with an aqueous saturated sodium bicarbonate solution and, then, twice with an aqueous saturated sodium chloride solution. The washed solvent phase was dried over anhydrous magnesium sulfate. Thereafter, the solvent phase was concentrated in vacuo to obtain an oily residue. The oily residue thus obtained was adsorbed into a column packed with 30 g of silica gel (i.e., CC-7 manufactured by Mallinckrodt, Inc. and, then, was eluted with a mixture of benzene and ethyl acetate (9:11). Thus, the desired compounds in the form of colorless amorphous powder were obtained.

The structures and the physico-chemical data of the compound Nos. 1 to 17 and 100 to 104 thus obtained are shown in Table 1.

TABLE 1

| Compound No. | 1 | 2 | 3 | 4 |
|---|---|---|---|---|
| R | $-\overset{O}{\underset{\|}{C}}-(CH_2)_8CH_3$ | $-\overset{O}{\underset{\|}{C}}-(CH_2)_{11}CH_3$ | $-\overset{O}{\underset{\|}{C}}-(CH_2)_{14}CH_3$ | $-\overset{O}{\underset{\|}{C}}-(CH_2)_{20}CH_3$ |
| Specific rotatory power $[\alpha]_D^{26-28°C.}$ (CHCl$_3$) | −8.3° (C = 0.12) | −11.9° (C = 1.54) | −10.2° (C = 1.01) | −8.6° (C = 1.15) |
| Infrared absorption (KBr, cm$^{-1}$) | 1760, 1758, 1742, 1690 | 1760, 1758, 1745, 1690 | 1760, 1758, 1742, 1690 | 1760, 1758, 1742, 1690 |
| Elemental analysis | | | | |
| Molecular formula | C$_{36}$H$_{48}$O$_{12}$ | C$_{39}$H$_{54}$O$_{12}$ | C$_{42}$H$_{60}$O$_{12}$ | C$_{48}$H$_{72}$O$_{12}$ |
| Calc. (C, H) % | 64.27, 7.19 | 65.53, 7.61 | 66.64, 7.99 | 68.54, 8.63 |
| Found (C, H) % | 64.19, 7.10 | 65.61, 7.59 | 66.51, 7.79 | 68.44, 8.70 |

| Compound No. | 5 | 6 | 7 | 8 |
|---|---|---|---|---|
| R | $-\overset{O}{\underset{\|}{C}}-\underset{\underset{CH_2(CH_2)_4CH_3}{\|}}{CH}(CH_2)_7CH_3$ | $-\overset{O}{\underset{\|}{C}}-\underset{\underset{CH_2CH_3}{\|}}{CH}(CH_2)_3CH_3$ | $-\overset{O}{\underset{\|}{C}}-CH_2-\underset{\underset{CH_3}{\|}}{CH}-CH_2-C(CH_3)_3$ | $\underset{-\overset{\|}{\underset{O}{C}}}{}\overset{H}{\underset{CH_3}{\diagdown C=C \diagup}}\overset{(CH_2)_2CH_3}{}$ |
| Specific rotatory power $[\alpha]_D^{26-28°C.}$ (CHCl$_3$) | −7.0° (C = 0.53) | −14.0° (C = 0.20) | −12.3° (C = 0.44) | −18.0° (C = 0.30) |
| Infrared absorption (KBr, cm$^{-1}$) | 1765, 1760, 1750, 1740, 1730 | 1750, 1740, 1690, 1680 | 1765, 1760, 1755, 1745, 1740 | 1760, 1740, 1690, 1680 |
| Elemental analysis | | | | |
| Molecular formula | C$_{42}$H$_{60}$O$_{12}$ | C$_{34}$H$_{44}$O$_{12}$ | C$_{35}$H$_{46}$O$_{12}$ | C$_{33}$H$_{40}$O$_{12}$ |
| Calc. (C, H) % | 66.64, 7.99 | 63.34, 6.88 | 63.81, 7.04 | 63.00, 6.41 |
| Found (C, H) % | 66.73, 8.05 | 63.23, 7.01 | 63.73, 8.15 | 62.98, 6.35 |

| Compound No. | 9 | 10 | 11 | 12 |
|---|---|---|---|---|
| R | $\underset{-\overset{\|}{\underset{O}{C}}}{}\overset{H}{\underset{CH_3}{\diagdown C=C \diagup}}\overset{(CH_2)_4CH_3}{}$ | $\underset{-\overset{\|}{\underset{O}{C}}}{}\overset{H}{\underset{CH_3}{\diagdown C=C \diagup}}\overset{(CH_2)_6CH_3}{}$ | $\underset{-\overset{\|}{\underset{O}{C}}}{}\overset{H}{\underset{CH_3}{\diagdown C=C \diagup}}\overset{(CH_2)_8CH_3}{}$ | $\underset{-\overset{\|}{\underset{O}{C}}}{}\overset{H}{\underset{CH_3}{\diagdown C=C \diagup}}\overset{(CH_2)_{10}CH_3}{}$ |
| Specific rotatory power $[\alpha]_D^{26-28°C.}$ (CHCl$_3$) | −6.15° (C = 0.13) | −13.8° (C = 0.48) | −13.1° (C = 0.32) | −12.9° (C = 0.31) |
| Infrared absorption (KBr, cm$^{-1}$) | 1760, 1750, 1740, 1690, 1680 | 1765, 1760, 1755, 1750, 1730 | 1765, 1760, 1758, 1740, 1730 | 1770, 1760, 1750, 1735, 1729 |
| Elemental analysis | | | | |
| Molecular formula | C$_{35}$H$_{44}$O$_{12}$ | C$_{37}$H$_{48}$O$_{12}$ | C$_{39}$H$_{52}$O$_{12}$ | C$_{41}$H$_{56}$O$_{12}$ |
| Calc. (C, H) % | 64.01, 6.75 | 64.89, 7.07 | 65.71, 7.35 | 66.46, 7.62 |
| Found (C, H) % | 63.89, 6.73 | 64.78, 7.11 | 65.65, 7.20 | 66.31, 7.49 |

| Compound No. | 13 | 14 | 15 | 16 |
|---|---|---|---|---|
| R | (polyunsaturated acyl structure) | (polyunsaturated acyl structure) | (polyunsaturated acyl structure) | (polyunsaturated acyl structure) |
| Specific rotatory power $[\alpha]_D^{26-28°C.}$ (CHCl$_3$) | −17.8° (C = 0.18) | −15.4° (C = 0.13) | −3.95° (C = 0.43) | −21.8° (C = 0.28) |

TABLE 1-continued

| Infrared absorption (KBr, cm$^{-1}$) | 1760, 1750, 1740, 1690 | 1760, 1750, 1690, 1680 | 1760, 1750, 1740, | 1760, 1740, 1730, 1690, 1680 |
|---|---|---|---|---|
| Elemental analysis | | | | |
| Molecular formula | $C_{36}H_{44}O_{12}$ | $C_{36}H_{44}O_{12}$ | $C_{41}H_{52}O_{12}$ | $C_{41}H_{52}O_{12}$ |
| Calc. (C, H) % | 64.70, 6.63 | 64.70, 6.63 | 66.83, 7.11 | 66.83, 7.11 |
| Found (C, H) % | 64.49, 6.63 | 64.53, 6.70 | 66.65, 7.03 | 66.57, 6.99 |

| Compound No. | 17 | 100 | 101 |
|---|---|---|---|
| R | (structure: terpenoid acyl group) | $-\overset{O}{\underset{\|}{C}}-\overset{NHCO_2tBu}{\underset{\|}{CH}}-(CH_2)_5-CH_3$ | $-\overset{O}{\underset{\|}{C}}-\overset{NHCO_2tBu}{\underset{\|}{CH}}-(CH_2)_5-CH_3$ |
| | | (2'-S) | (2'-R) |
| Specific rotatory power $\alpha_D^{26-28°C}$ (CHCl$_3$) | 0° (C = 0.16) | −5.0° (C = 0.16) | 0° (C = 0.26) |
| Infrared absorption (KBr, cm$^{-1}$) | 1760, 1740, 1690, 1680 | 1760, 1750, 1720 1700, 1690 | 1750, 1740, 1720 1700, 1690, 1680 |
| Elemental analysis | | | |
| Molecular formula | $C_{46}H_{56}O_{12}$ | $C_{39}H_{53}O_{14}N$ | $C_{39}H_{53}O_{14}N$ |
| Calc. (C, H) % | | 61.64, 7.03 | 61.64, 7.03 |
| Found (C, H) % | | 61.31, 6.98 | 61.39, 7.21 |

| Compound No. | 102 | 103 | 104 |
|---|---|---|---|
| R | $-\overset{O}{\underset{\|}{C}}-\overset{NHCO_2tBu}{\underset{\|}{CH}}CH_2CH\overset{CH_3}{\underset{CH_3}{}}$ | $-\overset{O}{\underset{\|}{C}}-\overset{OCH_2OCH_3}{\underset{\|}{CH}}-(CH_2)_6-CH_3$ | $-\overset{O}{\underset{\|}{C}}-\overset{OCH_2OCH_3}{\underset{\|}{CH}}-(CH_2)_{11}-CH_3$ |
| | (2'-S,L—Leucine) | (2'-R,2'-S mixture) | (2'-R,2'-S mixture) |
| Specific rotatory power $\alpha_D^{26-28°C}$ (CHCl$_3$) | −20.5° (C = 0.21) | −5.71° (C = 0.21) | −9.00° (C = 0.10) |
| Infrared absorption (KBr, cm$^{-1}$) | 1760, 1750, 1710 1690 | 1750, 1740, 1690 1680 | 1750, 1740, 1690 |
| Elemental analysis | | | |
| Molecular formula | $C_{37}H_{49}O_{14}N$ | $C_{37}H_{50}O_{14}$ | $C_{42}H_{60}O_{14}$ |
| Calc. (C, H) % | 60.72, 6.75 | 61.82, 7.01 | 63.94, 7.67 |
| Found (C, H) % | 60.74, 6195 | 62.00, 7.15 | 63.93, 7.83 |

EXAMPLE 2

Synthesis No. 2 of Triacetyl Compound (9) ($R_1$=COCH$_3$) (i.e., 15β-hydroxyailanthone triacetate-carboxylic acid esters)

A carboxylic acid (3.2 mM, 1.6 equivalent) and 809 mg (3.8 mM, 1.9 equivalent) of 1-ethyl-2-fluoropyridinium tetrafluoroborate were dissolved in 10 ml of methylene chloride and, then, 1.74 g (11 mM, 5.7 equivalent) of cesium fluoride was added thereto. The resultant solution was stirred at room temperature for 30 minutes.

Then, 1.036 g (2 mM) of 15-hydroxyailanthone triacetate (i.e., the compound (8): $R_1$=COCH$_3$) was dissolved in 20 ml of methylene chloride. To the resultant solution, the above-prepared solution was added by decantation. Thereafter, 1.74 g (11 mM, 5.7 equivalent) of cesium fluoride and 100 mg of 4-dimethylaminopyridine were added to the solution and the mixture was allowed to stand at room temperature for 3 hours while stirring. The reaction mixture was washed twice with water and, then, once with an aqueous saturated sodium chloride solution, followed by drying over anhydrous magnesium sulfate. The solvent phase was concentrated in vacuo to obtain the oily residue. The oily residue was adsorbed into a column packed with 105 ml of silica gel (Kieselgel 60 having a size of 230–400 mesh manufactured by Merck & Co. Inc.) and, then, was eluted with a mixture of n-hexane and ethyl acetate (1:1.2) under pressure with nitrogen gas. After distillating the solvent in vacuo, the desired compounds in the form of colorless powder were obtained.

The structures and the physico-chemical data of the compound Nos. 18 to 25 thus obtained are shown in Table 2.

TABLE 2

| Compound No. | 18 | 19 | 20 | 21 |
|---|---|---|---|---|
| R | (acyl group with OCH$_2$OCH$_2$CH$_2$OCH$_3$) | (acyl group with OCH$_2$OCH$_3$) | (acyl group) | (acyl group) |
| Specific rotatory power $[\alpha]_D^{26-28°C}$ (CHCl$_3$) | +10.8° (C = 0.85) | +8.9° (C = 0.28) | +11.9° (C = 0.33) | +6.9° (C = 0.29) |
| Infrared absorption | 1745, 1720, 1670 | 1750, 1724, 1684, | 1760, 1695, 1640 | 1760, 1730, 1680, |

TABLE 2-continued

| (KBr, cm$^{-1}$) | 1644 | | 1655 |
|---|---|---|---|
| Elemental analysis | | | |
| Molecular formula | $C_{37}H_{48}O_{15}$ | $C_{35}H_{44}O_{14}$ | $C_{34}H_{42}O_{12}$ | $C_{34}H_{42}O_{12}$ |
| Calc. (C, H)% | 60.64, 6.60 | 61.04, 6.44 | 63.54, 6.59 | 63.54, 6.59 |
| Found (C, H)% | 60.78, 6.72 | 61.25, 6.32 | 63.62, 6.63 | 63.52, 6.51 |

| Compound No. | 22 | 23 | 24 | 25 |
|---|---|---|---|---|
| R | (acyl group) | (acyl group) | (acyl group) | (cinnamoyl group) |
| Specific rotatory power $[\alpha]_D^{26-28°C}$ (CHCl$_3$) | | +12.4° (C = 0.19) | +23.10° (C = 0.09) | −1.7° (C = 0.46) |
| Infrared absorption (KBr, cm$^{-1}$) | 1750, 1720, 1680 | 1750, 1720, 1680, 1640 | 1760, 1740, 1690 | 1751, 1686, 1633, |
| Elemental analysis | | | | |
| Molecular formula | $C_{35}H_{44}O_{12}$ | $C_{36}H_{46}O_{12}$ | $C_{34}H_{40}O_{12}$ | $C_{35}H_{36}O_{12}$ |
| Calc. (C, H)% | 64.01, 6.75 | 64.46, 6.91 | 63.74, 6.29 | 64.81, 5.59 |
| Found (C, H)% | 64.13, 6.82 | 64.37, 7.00 | 63.63, 6.20 | 64.75, 5.46 |

EXAMPLE 3

Synthesis No. 3 of Triacetyl Compound (9) ($R_1$=COCH$_3$) (i.e., 15β-hydroxyailanthone triacetate-carboxylic acid esters)

A 600 mg amount (1.16 mM) of 15β-hydroxyailanthone triacetate (i.e., the compound (8): $R_1$=COCH$_3$) and a carboxylic acid anhydride (2.7 equivalent) prepared in a conventional manner were dissolved in 60 ml of anhydrous methylene chloride. A 1.6 g (10 equivalent) amount of anhydrous potassium carbonate was added to the solution and the mixture was allowed to stand one night at room temperature while stirring. After adding a saturated aqueous sodium bicarbonate solution to the reaction mixture, the mixture was stirred for 3 minutes. The reaction mixture was, then, extracted four times with methylene chloride.

The methylene chloride phase was washed with a saturated aqueous sodium bicarbonate solution, water, and a saturated aqueous sodium chloride solution, in this order and, then, was dried over anhydrous magnesium sulfate. The solvent phase was concentrated in vacuo to obtain an oily residue. The oily residue was adsorbed into a column packed with 290 ml of silica gel (Kieselgel 60 having a size of 230–400 mesh manufactured by Merck & Co., Inc.) and, then, was eluted with a mixture of n-hexane and ethyl acetate (1:1) under pressure with nitrogen gas. After distilling the solvent in vacuo, the desired compounds in the form of colorless powder were obtained.

The structures and the physico-chemical data of the compound Nos. 26 to 35 thus obtained are shown in Table 3.

TABLE 3

| Compound No. | 26 | 27 | 28 |
|---|---|---|---|
| R | (acyl group) | (acyl group) | (acyl group) |
| Specific rotatory power $[\alpha]_D^{26-28°C}$ (CHCl$_3$) | −14.3° (C = 0.40) | −11.5° (C = 0.55) | +15° (C = 0.20) |
| Infrared absorption (KBr, cm$^{-1}$) | 1760, 1740, 1730, 1690, 1680 | 1760, 1740, 1730 | 1750, 1685, 1640 |
| Elemental analysis | | | |
| Molecular formula | $C_{33}H_{40}O_{12}$ | $C_{35}H_{44}O_{12}$ | $C_{36}H_{46}O_{12}$ |
| Calc. (C, H)% | 63.00, 6.41 | 64.01, 6.75 | 64.46, 6.91 |
| Found (C, H)% | 62.87, 6.46 | 63.86, 6.61 | 64.33, 7.00 |

| Compound No. | 29 | 30 | 31 | 32 |
|---|---|---|---|---|
| R | (acyl group) | (acyl group) | (acyl group) | (acyl group) |
| Specific rotatory power $[\alpha]_D^{26-28°C}$ (CHCl$_3$) | +13° (C = 0.52) | −13.2° (C = 0.22) | −13.0° (C = 0.92) | −2.4° (C = 0.25) |
| Infrared absorption (KBr, cm$^{-1}$) | 1750, 1690, 1640 | 1760, 1750, 1742, 1730 | 1765, 1760, 1750, 1740, 1730 | 1750, 1710, 1680 |
| Elemental analysis | | | | |
| Molecular formula | $C_{37}H_{48}O_{12}$ | $C_{39}H_{52}O_{12}$ | $C_{42}H_{58}O_{12}$ | $C_{31}H_{36}O_{12}$ |
| Calc. (C, H)% | 64.89, 7.07 | 65.71, 7.35 | 66.82, 7.74 | 62.00, 6.04 |

TABLE 3-continued

| Found (C, H)% | 64.68, 7.02 | 65.60, 7.52 | 66.74, 7.68 | 62.10, 6.20 |
|---|---|---|---|---|
| Compound No. | 33 | 34 | 35 | |
| R | (C(=O)- with branched methyl alkenyl chain) | (C(=O)- with branched methyl alkenyl chain) | (C(=O)- with branched methyl alkenyl chain) | |
| Specific rotatory power $[\alpha]_D^{26-28°C}$ (CHCl$_3$) | +6.3° (C = 0.16) | +6.2° (C = 0.19) | +3.7° (C = 0.46) | |
| Infrared absorption (KBr, cm$^{-1}$) | 1755, 1695, 1655 | 1760, 1720, 1680 | 1753, 1712, 1671 | |
| Elemental analysis | | | | |
| Molecular formula | C$_{35}$H$_{44}$O$_{12}$ | C$_{37}$H$_{48}$O$_{12}$ | C$_{41}$H$_{56}$O$_{12}$ | |
| Calc. (C, H)% | 64.01, 6.75 | 64.89, 7.07 | 66.46, 7.62 | |
| Found (C, H)% | 63.85, 6.91 | 64.72, 7.23 | 66.38, 7.51 | |

EXAMPLE 4

Synthesis No. 4 of Triacetyl Compound (9) (R$_1$=COCH$_3$) (i.e., 15β-hydroxyailanthone triacetate-carboxylic acid esters)

A 518 mg amount (1.0 mM) of 15β-hydroxailanthone triacetate (i.e., the compound (8): R$_1$=COCH$_3$) and a carboxylic acid anhydride (3.0 equivalent) prepared in a conventional manner were dissolved in 20 ml of anhydrous methylene chloride. A 303 mg (3.0 equivalent) amount of triethylamine was added to the solution and the mixture was allowed to stand for 6 hours at room temperature while stirring.

The reaction mixture thus obtained was concentrated in vacuo to obtain the oily residue. The oily residue was adsorbed into a column packed with 70 g of silica gel (Kieselgel 60 having a size of 70–230 mesh manufactured by Merck & Co., Inc.) and, then, was eluted with a mixture of benzene and ethyl acetate (1:4). After distillating the solvent in vacuo, the desired compounds in the form of colorless powder were obtained.

The structures and the physico-chemical data of the compound Nos. 36 to 41 thus obtained are shown in Table 4.

TABLE 4

| Compound No. | 36 | 37 | 38 |
|---|---|---|---|
| R | -C(=O)-phenyl | -C(=O)-phenyl-propyl | -C(=O)-phenyl-butyl |
| Specific rotatory power $[\alpha]_D^{26-28°C}$ (CHCl$_3$) | +20.4° (C = 0.29) | +11.0° (C = 0.30) | +7.7° (C = 0.43) |
| Infrared absorption (KBr, cm$^{-1}$) | 1750, 1690, 1630 | 1760, 1698, 1615 | 1760, 1690, 1615 |
| Elemental analysis | | | |
| Molecular formula | C$_{33}$H$_{34}$O$_{12}$ | C$_{37}$H$_{43}$O$_{12}$ | C$_{38}$H$_{45}$O$_{12}$ |
| Calc. (C, H)% | 63.66, 5.50 | 65.38, 6.38 | 65.79, 6.54 |
| Found (C, H)% | 63.51, 5.37 | 65.43, 6.39 | 65.58, 6.40 |
| Compound No. | 39 | 40 | 41 |
| R | -C(=O)- branched alkyl (mixture of 2'-R & 2'-S) | -C(=O)- branched alkyl (mixture of 2'-R & 2'-S) | -C(=O)- branched alkyl (mixture of 2'-R & 2'-S) |
| Specific rotatory power $[\alpha]_D^{26-28°C}$ (CHCl$_3$) | −11.1° (C = 0.39) | −11.2° (C = 0.29) | −2.6° (C = 0.11) |
| Infrared absorption (KBr, cm$^{-1}$) | 1760, 1748, 1738, 1690 | 1760, 1748, 1740, 1692 | 1760, 1748, 1740, 1690 |
| Elemental analysis | | | |
| Molecular formula | C$_{35}$H$_{46}$O$_{12}$ | C$_{37}$H$_{50}$O$_{12}$ | C$_{41}$H$_{58}$O$_{12}$ |
| Calc. (C, H)% | 63.81, 7.04 | 64.70, 7.34 | 66.28, 7.87 |
| Found (C, H)% | 63.83, 7.00 | 64.59, 7.34 | 66.18, 7.80 |

EXAMPLE 5

Synthesis of 15β-(3',4'-dimethyl-4'-hydroxy-2'-pentenoyl)oxyailanthone triacetate)

A 2.78 g (3.8 mM) amount of 15β-(3',4'-dimethyl-4'-methoxyethoxymethyloxy-2'-pentenoyl oxyailanthone triacetate prepared in Example 2 was dissolved in 39 ml of anhydrous methylene chloride and, then, 4.8 g of zinc bromide was added under a nitrogen gas atmosphere. The mixture was allowed to stand at room temperature for 5 hours while stirring. To the reaction mixture, methylene chloride was added. The methylene chloride portion was washed with water, a saturated aqueous sodium bicarbonate solution, and a saturated aqueous sodium chloride solution in this order and, then, was dried over anhydrous magnesium sulfate.

After the solvent was distilled off in vacuo, 2.57 g of the desired compound was obtained.

The structure and the physico-chemical data of the compound No. 42 thus obtained are as follows:

was adsorbed into a column packed with 290 ml of silica gel (Kieselgel 60 having a size of 230–400 mesh manufactured by Merck & Co., Inc.) and, then, was eluted with a mixture of n-hexane and ethyl acetate (1:2) under pressure with nitrogen gas. After distilling the solvent in vacuo, the desired compounds in the form of colorless powder were obtained.

The structures and the physico-chemical data of the compound Nos. 43 to 45 thus obtained are shown in Table 5.

TABLE 5

| Compound No. | 43 | 44 | 45 |
|---|---|---|---|
| R | (structure with OCCH₃) | (structure with OCCH₂CH₃) | (structure with OCCH₂CH₂CH₃) |
| Specific rotatory power $[\alpha]_D^{26-28°C.}$ (CHCl₃) | — | +9.3° (C = 0.30) | — |
| Infrared absorption (KBr, cm⁻¹) | 1750, 1695, 1650 | 1750, 1695, 1650 | 1750, 1690, 1650 |
| Elemental analysis | | | |
| Molecular formula | C₃₅H₄₂O₁₄ | C₃₆H₄₄O₁₄ | C₃₇H₄₆O₁₄ |
| Calc. (C, H)% | 61.21, 6.17 | 61.70, 6.33 | 62.17, 6.49 |
| Found (C, H)% | 61.38, 6.05 | 61.44, 6.45 | 62.18, 6.32 |

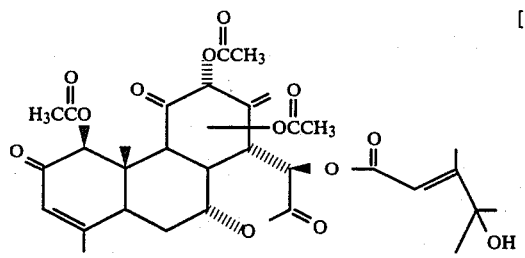

[1]

Specific rotatory power $[\alpha]_D^{26°-28°\ C.}$ (CHCl₃): +14.2°(C=0.25).

Infrared absorption (KBr, cm⁻¹): 1755, 1690, 1650.
Elemental analysis

| Molecular formula: | C₃₃H₄₀O₁₃ | |
|---|---|---|
| Calc. (C, H) % | 61.48 | 6.25 |
| Found (C, H) % | 61.63 | 6.18 |

EXAMPLE 6

Synthesis of 15β-(3',4'-dimethyl-4'-acyloxy-2'-pentenoyl)oxyailanthone triacetate)

A 1.25 g (1.9 mM) amount of 15β-(3',4'-dimethyl-4'-hydroxy-2'-pentenoyl)oxyailanthone triacetate was dissolved in 300 mg (1.6 equivalent) of triethylamine and 3 equivalents of the acid anhydride of linear saturated fatty acid. Then, 70 mg of 4-dimethylaminopyridine was added thereto. The mixture was stirred at room temperature for 2.5 hours.

Ether was added to the reaction mixture. The ether solution was washed with 2N hydrochloric acid (twice), an aqueous saturated sodium bicarbonate solution (once), water (once), and an aqueous saturated sodium chloride solution (twice) and, then, was dried over anhydrous magnesium sulfate. The solvent phase was concentrated in vacuo. The residue thus obtained

EXAMPLE 7

Synthesis of 15β-hydroxyailanthone-carboxylic acid esters (i.e., the compound (1)) according to the present invention A 1.0 mM amount of the triacetylailanthone-carboxylic acid ester obtained in Examples 1 to 6 was dissolved in a methanol solution of potassium methoxide (0.85 equivalent) and, then, was allowed to stand at room temperature for 2 hours under a nitrogen atmosphere while stirring.

After the reaction, 1N hydrochloric acid was added to the reaction mixture to adjust the pH thereof to 4 to 5. The methanol was distilled off and, then, water was added to the residue. The resultant mixture was extracted three times with methylene chloride. The methylene chloride layer thus separated was washed twice with a saturated aqueous sodium chloride solution. The solvent was removed from the dried extract in vacuo. The residue was adsorbed into a column packed with silica gel (Kieselgel 60 having a size of 70–230 mesh manufactured by Merck & Co., Inc.) and, then, was eluted with a mixture of ethyl acetate and n-hexane (5:2). After distillating the solvent in vacuo, the desired compounds in the form of colorless amorphous powder were obtained.

The structures and the physico-chemical data of the compound Nos. 46 to 91 thus obtained are shown in Table 6.

Furthermore, the mixture of the monoacetate compound and the diacetate compound separated in the silica gel column was again acylated at room temperature in a mixture ten times the amount of anhydrous pyridine and twenty times the amount of acetic anhydride for 48 hours while stirring and, then, was hydrolyzed in the same manner as mentioned above. Thus, the desired compound (1) was recovered.

TABLE 6

| | Compound No. | | | | | |
|---|---|---|---|---|---|---|
| | 46 | 47 | 48 | 49 | 50 | 51 |
| R | −C(=O)−(CH₂)₈CH₃ | −C(=O)−(CH₂)₁₁CH₃ | −C(=O)(CH₂)₁₄CH₃ | −C(=O)(CH₂)₂₀CH₃ | −C(=O)−CH(CH₂)₇CH₃ / CH₂(CH₂)₄CH₃ | −C(=O)−CH(CH₂)₃CH₃ / CH₂CH₃ |
| Specific rotatory power [α]$_D^{26-28°C}$ (CHCl₃) | +31.9° (C = 0.16) | +15.7° (C = 0.14) | +24.0° (C = 0.10) | +21.8° (C = 0.11) | +32.12° (C = 0.66) | +42.6° (C = 0.19) |
| Infrared absorption (KBr, cm⁻¹) | 3400, 1760, 1740 | 3400, 2930, 1745, 1735, 1665 | 3400, 1760, 1740 | 3400, 1760, 1740 | 3400, 1765, 1760, 1745, 1690 | 3400, 1750, 1740, 1660 |
| Ultraviolet absorption (λ$_{max}^{EtOH}$, nm) | 237 (ε10300) | 237 (ε9300) | 237 (ε9900) | 240 (ε10400) | 238 (ε11300) | 237 (ε10500) |
| Mass spectrum (m/Z) | 546 (M⁺), 528, 502, 458 | 588 (M⁺), 500, 416, 344, 300 | 630 (M⁺), 612, 416, 344, 300 | 714 (M⁺), 696, 416, 344 | 630 (M⁺), 612, 542, 374, 330 | 518 (M⁺), 500, 474, 444 |
| Proton NMR (100 MHz, CDCl₃, δ in ppm; CHCl₃ chemical shift (δ7.24) was used as internal standard) | 0.88 (3H, t) 1.20 (3H, s) 1.27 (12H, s) 1.66 (2H, brs) 2.04 (2H, s) 2.29 (2H, m) 2.42 (2H, t) 2.86 (1H, d, J=12Hz) 3.04 (1H, s) 3.54, 3.92 (each 1H, d, J=8Hz) 4.05 (1H, s) 4.16 (1H, s) 4.60 (1H, t) 5.20, 5.38 (each 1H, s) 5.68 (1H, d, J=12Hz) 6.16 (1H, brs) | 0.88 (3H, t) 1.27 (18H, s) 1.65 (2H, brs) 2.42 (2H, t) The other signals exhibited the same shift values as in compound No. 46. | 0.88 (3H, t) 1.27 (24H, s) 1.62 (2H, brs) 2.42 (2H, t) The other signals exhibited the same shift values as in compound No. 46 | 0.88 (3H, t) 1.26 (36H, s) 1.60 (2H, brs) 2.42 (2H, t) The other signals exhibited the same shift values as in compound No. 46 | 0.84 (6H, t) 1.23−1.70 (24H, m) 2.40 (1H, m) The other signals exhibited the same shift values as in compound No. 46 | 0.90 (3H, t) 0.93 (3H, t) 1.30−1.70 (8H, m) 2.32 (1H, m) The other signals exhibited the same shift values as in compound No. 46 |
| Molecular formula | C₃₀H₄₂O₉ | C₃₃H₄₈O₉ | C₃₆H₅₄O₉ | C₄₂H₆₆O₉ | C₃₆H₅₄O₉ | C₂₈H₃₈O₉ |
| Elemental analysis Calc. (C, H) % | — | — | 68.54, 8.63 | 70.55, 9.30 | 68.54, 8.63 | 64.85, 7.39 |
| Found (C, H) % | — | — | 68.48, 8.50 | 70.63, 9.19 | 68.27, 8.70 | 65.01, 7.38 |
| High resolution power mass spectrum Calc. (m/Z) | 546.2826 | 588.3295 | — | — | — | — |
| Found (m/Z) | 546.2825 | 588.3287 | — | — | — | — |

| | Compound No. | | | | | |
|---|---|---|---|---|---|---|
| | 52 | 53 | 54 | 55 | 56 | |
| R | −C(=O)−CH₂−CHCH₂C(CH₃)₃ / CH₃ | H\\C=C/(CH₂)₂CH₃ , O=C / CH₃ | H\\C=C/(CH₂)₄CH₃ , O=C / CH₃ | H\\C=C/(CH₂)₆CH₃ , O=C / CH₃ | H\\C=C/(CH₂)₈CH₃ , O=C / CH₃ | |
| Specific rotatory power [α]$_D^{26-28°C}$ (CHCl₃) | +55.0° (C = 0.54) | +46.9° (C = 0.13) | +50.0° (C = 0.10) | +35.6° (C = 0.34) | +32.4° (C = 0.71) | |
| Infrared absorption (KBr, cm⁻¹) | 3400, 1765, 1760, 1755, 1740, 1730 | 3300, 1760, 1720 1660 | 3300, 1760, 1720 1660 | 3250, 1758, 1750, 1725 | 3250, 1758, 1750, 1735, 1720 | |
| Ultraviolet absorption (λ$_{max}^{EtOH}$, nm) | 237 (ε10800) | 225 (ε21400) | 227 (ε18900) | 227 (ε23100) | 226 (ε21300) | |
| Mass spectrum (m/Z) | 532 (M⁺), 499, 434, 374, 330 | 502 (M⁺), 484, 458, 428 | 530 (M⁺), 512, 486, 456 | 558 (M⁺), 540, 470, 347, 300 | 586 (M⁺), 374, 300, 267 | |

TABLE 6-continued

| | 57 | 58 | 59 | 60 | 60' |
|---|---|---|---|---|---|
| Proton NMR (100 MHz, CDCl₃, δ in ppm, CHCl₃ chemical shift (δ7.24) was used as internal standard) | 0.88 (9H, s) 0.99 (3H, d) 1.17 (6H, m) 2.24 (2H, m) The other signals exhibited the same shift values as in compound No. 46. | 0.91 (3H, t) 1.20 (3H, s) 1.50 (2H, m) 2.00 (3H, s) 2.15 (3H, s) 2.85 (1H, d, J=12Hz) 3.04 (1H, s) 3.54, 3.90 (each 1H, d, J=8Hz) 4.04 (1H, s) 4.12 (1H, s) 4.60 (1H, t) 5.17, 5.35 (each 1H, s) 5.66 (1H, d, J=12Hz) 5.73 (1H, s) 6.16 (1H, brs) The other signals exhibited the same shift values as in compound No. 53. | 0.88 (3H, t) 1.24–1.60 (6H, m) The other signals exhibited the same shift values as in compound No. 53. | 0.86 (3H, t) 1.25 (10H, m) The other signals exhibited the same shift values as in compound No. 53. | 0.86 (3H, t) 1.25 (14H, brs) The other signals exhibited the same shift values as in compound No. 53. |
| Molecular formula | C₂₉H₄₀O₉ | C₂₇H₃₄O₉ | C₂₉H₃₈O₉ | C₃₁H₄₂O₉ | C₃₃H₄₆O₉ |
| Elemental analysis Calc. (C, H) % | — | 64.53, 6.82 | 65.64, 7.22 | — | 67.55, 7.90 |
| Found (C, H) % | — | 64.51, 6.68 | 65.57, 7.10 | — | 67.69, 7.88 |
| High resolution power mass spectrum Calc. (m/Z) | 532.2669 | — | — | 558.2829 | — |
| Found (m/Z) | 532.2663 | — | — | 558.2840 | — |

| | Compound No. | | | | |
|---|---|---|---|---|---|
| | 57 | 58 | 59 | 60 | 60' |
| R | H, (CH₂)₁₀CH₃, CH₃ (C=C with O=C) | (geranyl-type acyl) | (geranyl-type acyl) | (farnesyl-type acyl) | (geranylgeranyl-type acyl) |
| Specific rotatory power [α]D²⁶⁻²⁸°C (CHCl₃) | +38.9° (C = 0.35) | +62.5° (C = 0.12) | +51.0° (C = 0.20) | +57.3° (C = 0.15) | +52.0° (C = 0.10) |
| Infrared absorption (KBr, cm⁻¹) | 3250, 1760, 1750, 1745, 1730, 1720 | 3300, 1760, 1720, 1660, 1650 | 3300, 1740, 1720, 1670 | 3300, 1740, 1720, 1660 | 3300, 1760, 1730, 1670, 1650 |
| Ultraviolet absorption (λmax^EtOH, nm) | 228 (ε24100) | 226 (ε24700) | 218 (ε19900) | 226 (ε24900) | 228 (ε19800) |
| Mass spectrum (m/Z) | 614 (M⁺), 570, 347, 330 | 542 (M⁺), 474 | 542 (M⁺), 524, 474, 456 | 610 (M⁺), 592, 568, 542, 474 | 610 (M⁺), 566, 474 |
| Proton NMR (100 MHz, CDCl₃, δ in ppm, CHCl₃ chemical shift (δ7.24) was used as internal standard) | 0.86 (3H, t) 1.23 (18H, brs) The other signals exhibited the same shift values as in compound No. 46. | 1.20 (3H, s) 1.60, 1.68 (each 3H, s) 2.01 (3H, s) 2.16 (3H, s) 2.86 (1H, d, J=12Hz) 3.04 (1H, s) 3.52, 3.90 (each 1H, d, J=8Hz) 4.04 (1H, s) 4.12 (1H, s) 4.58 (1H, t) | 1.58, 1.66 (each 3H, s) 1.92 (3H, s) 5.09 (1H, m) 5.73 (1H, s) The other signals exhibited the same shift values as in compound No. 58. | 1.57, 1.65 (each 3H, s) 2.15 (6H, s) 5.04 (2H, m) 5.72 (1H, s) The other signals exhibited the same shift values as in compound No. 58. | 1.57, 1.64 (each 3H, s) 1.89 (3H, s) 2.00 (6H, s) 5.08 (2H, m) 5.72 (1H, s) The other signals exhibited the same shift values as in compound No. 58. |

TABLE 6-continued

| | | Compound No. | | | | |
|---|---|---|---|---|---|---|
| | | 61 | 62 | 63 | 64 | 65 | 66 |

| | 61 | 62 | 63 | 64 | 65 | 66 |
|---|---|---|---|---|---|---|
| R | (structure shown: polyene chain with cyclohexenyl group and C=O) | O NHCOOt—Bu ‖ —C—CH(CH₂)₅CH₃ | O NHCOOt—Bu ‖ —C—CH(CH₂)₅CH₃ | O NHCOOiBu ‖ —C—CHCH₂CH(CH₃)₂ | O OCH₂OCH₃ ‖ —C—CH(CH₂)₆CH₃ | O OCH₂OCH₃ ‖ —C—CH(CH₂)₁₁CH₃ |
| Molecular formula | C₃₅H₅₀O₉ | C₃₀H₃₈O₉ | C₃₀H₃₈O₉ | C₃₅H₄₆O₉ | C₃₅H₄₆O₉ | C₃₅H₄₆O₉ |
| Elemental analysis | | | | | | |
| Calc. (C, H) % | 68.38, 8.20 | — | 66.40, 7.06 | 68.83, 7.59 | — | 68.83, 7.59 |
| Found (C, H) % | 68.35, 8.01 | — | 66.36, 7.09 | 68.92, 7.63 | — | 68.71, 7.46 |
| High resolution power mass spectrum | | | | | | |
| Calc. (m/Z) | — | 542.2513 | — | — | — | — |
| Found (m/Z) | — | 542.2501 | — | — | — | — |
| Specific rotatory power [α]$_D^{26-28°C.}$ (CHCl₃) | +74.5° (C = 0.11) | (2′-S) +33.0° (C = 0.20) | (2′-R′) +47.5° (C = 0.12) | (2′-S, L-Leucine) +25.4° (C = 0.13) | (2′-R + 2′-S) +35.7° (C = 0.14) | (2′-R + 2′-S) +37.4° (C = 0.31) |
| Infrared absorption (KBr, cm⁻¹) | 3300, 1760, 1720 1680 | 3300, 1760, 1700, 1690, 1680 | 3300, 1760, 1710, 1690, 1680 | 3300, 1760, 1720, 1690, 1680 | 3300, 1760, 1680 | 3300, 1760, 1670 |
| Ultraviolet absorption ($\lambda_{max}^{EtOH}$, nm) | 238 (ε17000) | 239 (ε10200) | 238 (ε10900) | 238 (ε10400) | 238 (ε10300) | 238 (ε10000) |
| Mass spectrum (m/Z) | 674 (M⁺), 656 | 633 (M⁺), 589, 533, 515 | 633 (M⁺), 615, 589, 533, 515 | 571, 487, 443, 395, (M⁺ not observed) | 592 (M⁺), 574, 548 504 | 662 (M⁺), 644, 618 600 |
| Proton NMR (100 MHz, CDCl₃, δ in ppm, CHCl₃ chemical shift (δ7.24) was used as internal standard) | (Determined at 360 MHz proton NMR) 1.03 (6H, s) 1.20 (3H, s) 1.71 (3H, s) 2.00 (3H, s) 2.02 (3H, s) 2.36 (3H, s) 2.97 (1H, d, J=12Hz) 3.08 (1H, s) 3.57, 3.93 (each 1H, d, J=8Hz) 4.07 (1H, s) 4.17 (1H, s) 4.63 (1H, t) 5.20, 5.38 (each 1H, s) 5.73 (1H, d, J=12Hz) 5.84 (1H, brs) 6.05–6.35 (4H, m) 7.05 (1H, dd, J=15Hz, 12Hz) | 0.85 (3H, t) 1.17 (3H, S) 1.25 (8H, brs) 1.43 (9H, S) 1.60 (2H, m) 2.00 (3H, S) 2.92 (1H, d, J=12Hz) 2.98 (1H, S) 3.54, 3.90 (each 1H, d, J=8Hz) 4.03 (1H, S) 4.12 (1H, S) 4.35 (1H, m) 4.59 (1H, t) 4.92 (1H, m) 5.24, 5.37 (each 1H, S) 5.56 (1H, d, J=12Hz) 6.16 (1H, t) | 0.85 (3H, t) 1.17 (3H, S) 1.28 (8H, m) 1.40 (9H, S) 1.61 (2H, m) 2.00 (3H, S) 2.27 (2H, m) 2.80 (1H, d, J=12Hz) 3.04 (1H, S) 3.53, 3.89 (each 1H, d, J=8Hz) 4.04 (1H, S) 4.15 (1H, S) 4.24 (1H, m) 4.37 (1H, t) 4.92 (1H, m) 5.22, 5.35 (each 1H, S) 5.76 (1H, d, J=12Hz) 6.14 (1H, brs) | 0.93 (6H, d, J=6Hz) 1.17 (3H, S) 1.43 (9H, S) 1.40–1.80 (3H, m) 2.00 (3H, S) 2.27 (2H, m) 2.91 (1H, d, J=12Hz) 2.98 (1H, S) 3.52, 3.88 (each 1H, d, J=8Hz) 4.02 (1H, S) 4.13 (1H, S) 4.35 (1H, m) 4.59 (1H, t) 4.82 (1H, d, J=8Hz) 5.23, 5.37 (each 1H, S) 5.56 (1H, d, J=12Hz) 6.13 (1H, brs) | One isomer 0.85 (3H, t) 1.17 (3H, S) 1.24 (10H, S) 1.74 (2H, brs) 2.00 (3H, S) 2.27 (2H, m) 3.34 (3H, S) 3.52, 3.90 (each 1H, d, J=8Hz) 4.03 (1H, S) 4.13 (1H, t, J=6Hz) 4.15 (1H, S) 5.20, 5.36 (each 1H, S) 5.76 (1H, d, J=12Hz) 6.14 (1H, brs) The other isomer 3.37 (3H, S) 4.21 (1H, t, J=6Hz) 5.66 (1H, d, J=12Hz) | One isomer 0.86 (3H, t) 1.23 (20H, S) 1.60 (2H, brs) 3.35 (3H, S) 4.13 (1H, t, J=6Hz) 5.76 (1H, d, J=12Hz) The other isomer 3.37 (3H, S) 4.22 (1H, t, J=6Hz) 5.67 (1H, d, J=12Hz) The other signals exhibited the same shift values as in compound No. 65. |
| | 5.05 (1H, m) 5.15, 5.33 (each 1H, s) 5.66 (1H, d, J=12Hz) 5.72 (1H, s) 6.13 (1H, brs) | | | | | |

TABLE 6-continued

| | Compound No. | | | | | |
|---|---|---|---|---|---|---|
| | 67 | 68 | 69 | 70 | 71 | 72 |
| R | (structure) | (structure) | (structure) | (structure) | (structure) | (structure) |
| Specific rotatory power $[\alpha]_D^{26-28°\ C.}$ (CHCl$_3$) | +59.2° (C = 0.12) | +60.0° (C = 0.11) | +55.7° (C = 0.42) | +65.1° (C = 0.38) | +45.4° (C = 0.28) | +52.0° (C = 0.10) |
| Infrared absorption (KBr, cm$^{-1}$) | 3300, 1750, 1730, 1670, 1640 | 3400, 1745, 1740, 1735, 1725 | 3400, 2920, 1760, 1680 | 3400, 1760, 1680 | 3400, 1755, 1740, 1723, 1720 | 3400, 1750, 1740, 1720, 1715 |
| Ultraviolet absorption ($\lambda_{max}^{EtOH}$, nm) | 225 (ε23000) | 225 (ε22200) | 226 (ε23400) | 226 (ε24400) | 225 (ε20900) | 224 (ε17300) |
| Mass spectrum (m/Z) | 502 (M$^+$), 458, 428 | 530 (M$^+$), 347, 247, 139 | 544 (M$^+$), 543, 525, 500, 344, 153 | 558 (M$^+$), 557, 539, 514, 344, 167 | 586 (M$^+$), 347, 330, 300, 267 | 628 (M$^+$), 610, 344, 300 |
| Proton NMR (100 MHz, CDCl$_3$, δ in ppm, CHCl$_3$ chemical shift (δ7.24) was used as internal standard) | 1.06 (6H, d, J=7Hz), 1.18 (3H, S), 2.00 (3H, S), 2.13 (3H, brs), 2.86 (1H, d, J=12Hz) 3.04 (1H, S) 3.54, 3.90 (each 1H, d, J=8Hz) 4.04 (1H, S) 4.15 (1H, S) 4.60 (1H, t) 5.16, 5.34 (each 1H, S) 5.66 (1H, d, J=12Hz) 5.72 (1H, S) 6.14 (1H, brs) | 0.88 (3H, t) 0.92 (3H, t) 1.40 (4H, m) 2.16 (3H, S) The other signals exhibited the same shift values as in compound No. 67. | 1.05 (3H, d, J=7Hz), 1.20 (3H, S), 1.25-1.50 (6H, m) 2.02 (3H, S) 2.10 (3H, S) 2.23 (1H, m) 2.36 (1H, m) 2.97 (1H, d, J=12Hz) 3.06 (1H, S) 3.56, 3.92 (each 1H, d, J=8Hz) 4.07 (1H, S) 4.15 (1H, S) 4.63 (1H, t) 5.18, 5.37 (each 1H, S) 5.70 (1H, d, J=12Hz) 5.75 (1H, brs) 6.17 (1H, brs) | 1.04 (3H, d, J=7Hz), 1.23-1.50 (8H, m) 2.10 (3H, S) 2.24 (1H, m) 5.75 (1H, brs) The other signals exhibited the same shift values as in compound No. 69. 0.87 (3H, t) | 1.03 (3H, d, J=7Hz), 1.24 (12H, S) 2.08 (3H, S) The other signals exhibited the same shift values as in compound No. 69. 0.87 (3H, t) | 1.02 (3H, d, J=7Hz), 1.24 (18H, S) 2.08 (3H, S) The other signals exhibited the same shift values as in compound No. 69. 0.86 (3H, t) |
| Molecular formula Elemental analysis | C$_{40}$H$_{50}$O$_9$ | | C$_{33}$H$_{47}$O$_{11}$N | C$_{33}$H$_{47}$O$_{11}$N | C$_{31}$H$_{43}$O$_{11}$N | C$_{36}$H$_{54}$O$_{11}$ |
| Calc. (C, H) % | — | — | 62.54, 7.48 | 62.54, 7.48 | 61.47, 7.16 | 65.23, 8.21 |
| Found (C, H) % | — | — | 62.61, 7.35 | 62.46, 7.50 | 61.60, 7.25 | 65.08, 8.10 |
| High resolution power mass spectrum | | | | | | |
| Calc. (m/Z) | — | 530.2514 | — | — | — | 592.2884 |
| Found (m/Z) | — | 530.2509 | — | — | — | 592.2907 |

| | Compound No. | | | | | |
|---|---|---|---|---|---|---|
| | 73 | 74 | 75 | 76 | 77 | 78 |
| Molecular formula Elemental analysis | C$_{27}$H$_{34}$O$_9$ | C$_{29}$H$_{38}$O$_9$ | C$_{30}$H$_{40}$O$_9$ | C$_{31}$H$_{42}$O$_9$ | C$_{33}$H$_{46}$O$_9$ | C$_{36}$H$_{52}$O$_9$ |
| Calc. (C, H) % | 64.53, 6.82 | — | 66.16, 7.40 | 66.65, 7.58 | 67.55, 7.90 | 68.76, 8.34 |
| Found (C, H) % | 64.72, 6.80 | — | 66.31, 7.58 | 66.49, 7.29 | 67.29, 7.81 | 68.63, 8.15 |
| High resolution power mass spectrum | | | | | | |
| Calc. (m/Z) | — | | — | — | — | — |
| Found (m/Z) | — | | — | — | — | — |

TABLE 6-continued

| R |  | 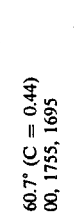 | 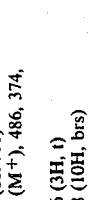 | 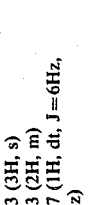 | 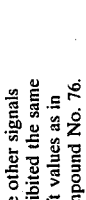 |  |
|---|---|---|---|---|---|---|
| Specific rotatory power $[\alpha]_D^{26-28^\circ C.}$ (CHCl$_3$) | +75.6° (C = 0.17) | +71.3° (C = 0.19) | +80.6° (C = 0.16) | +64.8° (C = 0.17) | +58.7° (C = 0.23) | +60.7° (C = 0.44) |
| Infrared absorption (KBr, cm$^{-1}$) | 3400, 1755, 1735, 1680 | 3400, 1760, 1730 1680 | 3480, 1760, 1730 1680 | 3300, 1755, 1715, 1680 | 3300, 1760, 1710 1675 | 3300, 1755, 1695 |
| Ultraviolet absorption ($\lambda_{max}^{EtOH}$, nm) | 232 (ε22500) | 241 (ε29200) | 241 (ε27600) | 219 (ε20600) | 225 (ε19600) | 225 (ε19700) |
| Mass spectrum (m/Z) | 496 (M$^+$), 424, 408 374 | 552 (M$^+$), 374, 330 | 566 (M$^+$), 547, 522, 344, 329 | 474 (M$^+$), 374, 330 | 530 (M$^+$), 486, 344 | 558 (M$^+$), 486, 374, 344 |
| Proton NMR (100 MHz, CDCl$_3$, δ in ppm, CHCl$_3$ chemical shift (δ7.24) was used as internal standard) | 1.20 (3H, s) 2.03 (3H, s) 2.39 (1H, s) 2.80 (1H, m) 3.01 (1H, d, J=12Hz) 3.10 (1H, s) 3.57, 3.94 (each 1H, d, J=8Hz) 4.06 (1H, s) 4.18 (1H, s) 4.66 (1H, t) 5.18, 5.32 (each 1H, s) 5.92 (1H, d, J=12Hz) 6.16 (1H, brs) 7.50 (3H, m) 8.06 (2H, dd, J=7Hz) | 0.91 (3H, t) 1.20 (3H, s) 1.50 (4H, s) 2.01 (3H, s) 2.36 (1H, m) 2.64 (2H, t) 2.88 (1H, s) 2.99 (1H, d, J=12Hz) 3.10 (1H, s) 3.56, 3.92 (each 1H, d, J=8Hz) 4.04 (1H, s) 4.17 (1H, s) 4.65 (1H, m) 5.16, 5.30 (each 1H, s) 5.98 (1H, d, J=12Hz) 6.14 (1H, brs) 7.21 (2H, d, J=8Hz) 7.94 (2H, d, J=8Hz) | 0.87 (3H, t) 1.20–1.80 (6H, m) 2.64 (2H, t) The other signals exhibited the same shift values as in compound No. 74. | 1.20 (3H, s) 1.82 (3H, d, J=7Hz) 1.86 (3H, s) 2.04 (3H, s) 2.38 (1H, m) 2.86 (1H, m) 2.92 (1H, d, J=12Hz) 3.07 (1H, s) 3.55, 3.92 (each 1H, d, J=8Hz) 4.06 (1H, s) 4.17 (1H, s) 4.63 (1H, m) 5.16, 5.37 (each 1H, s) 5.74 (1H, d, J=12Hz) 6.17 (1H, t) 7.00 (1H, q) | 0.88 (3H, t) 1.20–1.70 (6H, m) 1.84 (3H, s) 2.10 (2H, m) 7.87 (1H, dt, J=6Hz, 1Hz) The other signals exhibited the same shift values as in compound No. 76. | 0.86 (3H, t) 1.28 (10H, brs) 1.83 (3H, s) 2.13 (2H, m) 7.87 (1H, dt, J=6Hz, 1Hz) The other signals exhibited the same shift values as in compound No. 76. |
| Molecular formula | C$_{27}$H$_{28}$O$_9$ | C$_{31}$H$_{36}$O$_9$ | C$_{32}$H$_{38}$O$_9$ | C$_{25}$H$_{30}$O$_9$ | C$_{29}$H$_{38}$O$_9$ | C$_{31}$H$_{42}$O$_9$ |
| Elemental analysis Calc. (C, H) % | — | 67.38, 6.57 | 67.83, 6.77 | 63.28, 6.37 | — | 66.65, 7.58 |
| Found (C, H) % | — | 67.16, 6.63 | 67.61, 6.74 | 63.15, 6.18 | — | 66.72, 7.50 |
| High resolution power mass spectrum Calc. (m/Z) | 496.1730 | — | — | — | 530.2514 | — |
| Found (m/Z) | 496.1722 | — | — | — | 530.2514 | — |

| | Compound No. | | | | |
|---|---|---|---|---|---|
| | 79 | 80 | 81 | 82 | 83 |
| R |  | 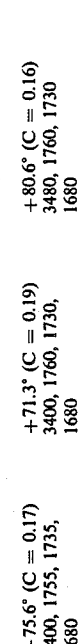 | 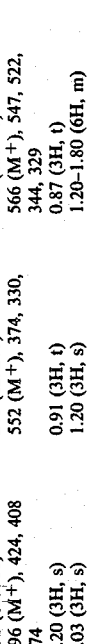 | 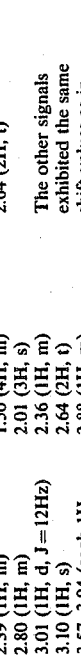 | 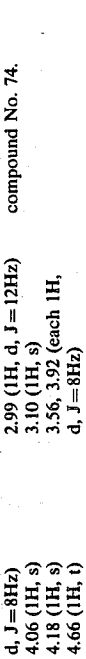 |
| Specific rotatory power $[\alpha]_D^{26-28^\circ C.}$ (CHCl$_3$) | +39.0° (C = 0.17) | +60.9° (C = 0.32) | +48.1° (C = 0.36) | +64.3° (C = 0.09) | +41.2° (C = 0.42) |
| Infrared absorption (KBr, cm$^{-1}$) | 3300, 1795, 1760 | 3400, 1740, 1675 | 3400, 1740, 1720, 1680, 1640 | 3400, 1745, 1675, 1640 | 3450, 1747, 1680, 1660 |
| Ultraviolet absorption ($\lambda_{max}^{EtOH}$, nm) | 225 (ε20000) | 225 (ε20900) | 224 (ε20600) | 235 (ε20500) | 225 (ε21000) |
| Mass spectrum (m/Z) | 614 (M$^+$), 344, 330 | 606 (M$^+$), 588, 530, 516, 500, 344 | 544, 500, 456, 406, (M$^+$ not observed) | 518 (M$^+$), 500, 430, 344 | 560 (M$^+$), 516, 500, 330 |

TABLE 6-continued

| | | | | |
|---|---|---|---|---|
| Proton NMR (100 MHz, CDCl₃, δ in ppm, CHCl₃ chemical shift (δ7.24) was used as internal standard) | 0.88 (3H, t), 1.27 (18H, brs), 1.86 (3H, s), 2.15 (2H, m), 7.79 (1H, dt, J=6Hz, 1Hz) The other signals exhibited the same shift values as in compound No. 76. | 1.20 (3H, s), 1.39 (6H, s), 2.01 (3H, s), 2.14 (3H, d, J=1Hz), 2.32 (1H, m), 2.79 (1H, m), 2.86 (1H, d, J=12Hz), 3.03 (1H, s), 3.36 (3H, s), 3.42–3.80 (5H, m), 3.90 (1H, d, J=8Hz), 4.04 (1H, s), 4.12 (1H, s), 4.60 (1H, t), 4.67 (2H, s), 5.16, 5.35 (each 1H, s), 5.68 (1H, d, J=12Hz), 5.98 (1H, d, J=1Hz), 6.16 (1H, brs) | 3.36 (3H, s), 4.57 (2H, s), 3.54, 3.92 (each 1H, s) The other signals exhibited the same shift values as in compound No. 80. | 3.54, 3.92 (each 1H, s) 6.17 (1H, d, J=1Hz) The other signals exhibited the same shift values as in compound No. 80. | 1.54 (6H, s), 2.02 (6H, s), 2.12 (3H, d, J=1Hz), 5.88 (1H, d, J=1Hz) The other signals exhibited the same shift values as in compound No. 81. |
| Molecular formula Elemental analysis | C₃₅H₅₀O₉ | C₃₁H₄₂O₁₂ | C₂₉H₃₈O₁₁ | C₂₇H₃₄O₁₀ | C₂₉H₃₆O₁₁ |
| Calc. (C, H) % Found (C, H) % | 68.38, 8.20 68.43, 8.15 | 61.37, 7.00 61.45, 7.20 | 61.91, 6.81 61.44, 6.78 | 62.53, 6.61 62.41, 6.75 | 62.13, 6.47 62.32, 6.38 |
| High resolution power mass spectrum Calc. (m/Z) Found (m/Z) | — | — | — | — | — |

| | Compound No. | | | | |
|---|---|---|---|---|---|
| | 84 | 85 | 86 | 87 | 88 |
| R | (structure) | (structure) | (structure) | (structure) | (structure) |
| Specific rotatory power [α]D²⁶⁻²⁸°C (CHCl₃) | +51.2° (C=0.66) | +48.3° (C=0.37) | +54.2° (C=0.36) | +55.7° (C=0.47) | +52.8° (C=0.35) |
| Infrared absorption (KBr, cm⁻¹) | 3400, 1745, 1720, 1680 | 3420, 1745, 1670, 1650 | 3400, 1743, 1665, 1635 | 3400, 1750, 1730, 1670 | 3400, 1750, 1665, 1645 |
| Ultraviolet absorption (λmax^EtOH, nm) | 226 (ε20700) | 226 (ε21800) | 225 (ε23000) | 226 (ε23900) | 226 (ε23000) |
| Mass spectrum (m/Z) | 574 (M⁺), 572, 556, 530, 500 | 588 (M⁺), 570, 500, 344 | 516 (M⁺), 500, 374, 344 | 516 (M⁺), 498, 444, 348 | 530 (M⁺), 344, 330 |
| Proton NMR (100 MHz, CDCl₃, δ in ppm, CHCl₃ chemical shift (δ7.24) was used as internal standard) | 1.10 (3H, t), 1.52 (6H, s), 2.28 (2H, q) The other signals exhibited the same | 0.93 (3H, t), 1.52 (6H, s), 1.30–1.70 (2H, m), 2.24 (2H, t) The other signals exhibited the same | (300 MHz, PMR: CHCl₃, δ7.24) 1.11 (9H, s), 1.21 (3H, s), 2.03 (3H, s), 2.17 (3H, d, J=1Hz), 2.37 (1H, m) | 0.88 (6H, d, J=7Hz), 1.20 (3H, s), 2.01 (3H, s), 2.14 (3H, d, J=1Hz), 2.32 (1H, m), 2.85 (1H, d, J=12Hz), 2.96 (1H, m) | 0.90 (6H, d, J=6Hz), 1.20–1.68 (3H, m), 2.16 (3H, d, J=1Hz), 5.72 (1H, brs) |

TABLE 6-continued

| | | | |
|---|---|---|---|
| | shift values as in compound No. 81. | 2.89 (1H, m)<br>2.97 (1H, d, J=12Hz)<br>3.07 (1H, s)<br>3.57, 3.93 (each 1H, d, J=8Hz)<br>4.08 (1H, s)<br>4.16 (1H, s)<br>4.63 (1H, t)<br>5.21, 5.39 (each 1H, s)<br>5.68 (1H, d, J=12Hz)<br>5.83 (1H, d, J=1Hz)<br>6.18 (1H, brs) | 3.04 (1H, s)<br>3.52, 3.90 (each 1H, d, J=8Hz)<br>4.03 (1H, s)<br>4.13 (1H, s)<br>4.60 (1H, t)<br>5.15, 5.34 (each 1H, s)<br>5.66 (1H, d, J=12Hz)<br>5.70 (1H, brs)<br>6.14 (1H, brs) | The other signals exhibited the same shift values as in compound No. 87. |
| Molecular formula<br>Elemental analysis | $C_{31}H_{40}O_{11}$ | $C_{30}H_{38}O_{11}$ | $C_{28}H_{36}O_9$ | $C_{29}H_{38}O_9$ |
| Calc. (C, H) %<br>Found (C, H) % | 63.25, 6.85<br>63.21, 6.98 | 62.70, 6.67<br>62.81, 6.75 | 65.10, 7.02<br>64.92, 7.31 | — |
| High resolution power mass spectrum | | | | |
| Calc. (m/Z)<br>Found (m/Z) | — | — | 516.2359<br>516.2367 | 530.2516<br>530.2522 |

| | Compound No. | | |
|---|---|---|---|
| | 89 | 90 | 91 |
| R | (acyl with branched alkenyl chain, isoprenyl-type) | (acyl with terminal vinyl branched chain) | (cinnamoyl, Ph-CH=CH-C(=O)-) |
| Specific rotatory power $[\alpha]_D^{26-28°\,C.}$ (CHCl$_3$) | +52.3° (C = 0.41) | +46.2° (C = 0.26) | +74.4° (C = 0.27) |
| Infrared absorption (KBr, cm$^{-1}$) | 3400, 1760, 1695, 1650 | 3400, 1753, 1690, 1655 | 3400, 1740, 1720, 1670, 1640 |
| Ultraviolet absorption ($\lambda_{max}^{EtOH}$, nm) | 226 (ε23600) | 226 (ε22500) | 280 (ε22500)<br>223 (ε18900)<br>218 (ε19200) |
| Mass spectrum (m/Z) | 544 (M$^+$), 534, 500, 330 | 514 (M$^+$), 496, 470, 344, 330 | 522 (M$^+$), 504, 328 |
| Proton NMR<br>(100 MHz, CDCl$_3$,<br>δ in ppm,<br>CHCl$_3$ chemical shift (δ7.24)<br>was used as internal standard) | 0.87 (6H, d, J=7Hz,)<br>1.00–1.80 (5H, m)<br>2.15 (3H, d, J=1Hz)<br>5.72 (1H, brs)<br>The other signals exhibited the same shift values as in compound No. 87. | 1.20 (3H, s)<br>2.01 (3H, s)<br>2.10–2.28 (6H, m)<br>2.85 (1H, d, J=12Hz)<br>2.75 (1H, m)<br>3.04 (1H, s)<br>3.52, 3.90 (each 1H, d, J=8Hz)<br>4.04 (1H, s)<br>4.13 (1H, s)<br>4.59 (1H, t)<br>4.92, 5.02, 5.08 (2H)<br>5.16, 5.34 (each 1H, s)<br>5.66 (1H, d, J=12Hz) | 1.20 (3H, s)<br>2.03 (3H, s)<br>2.36 (1H, m)<br>2.93 (1H, d, J=12Hz)<br>2.94 (1H, m)<br>3.07 (1H, s)<br>3.55, 3.92 (each 1H, d, J=8Hz)<br>4.05 (1H, s)<br>4.16 (1H, s)<br>4.63 (1H, t)<br>5.20, 5.37 (each 1H, s)<br>5.79 (1H, d, J=12Hz)<br>6.15 (1H, brs)<br>6.46 (1H, d, J=16Hz) |

TABLE 6-continued

|  |  |  |
|---|---|---|
|  |  | 5.73 (1H, brs) |
|  |  | 5.48–6.04 (1H, m) |
|  |  | 6.14 (1H, d, J=12Hz) |
|  |  | 7.40 (3H, m) |
|  |  | 7.46 (2H, m) |
|  |  | 7.76 (1H, d, J=16Hz) |
| Molecular formula | $C_{30}H_{40}O_9$ | $C_{28}H_{34}O_9$ | $C_{29}H_{30}O_9$ |
| Elemental analysis |  |  |  |
| Calc. (C, H) % | 66.16, 7.40 | 65.35, 6.66 | 66.65, 5.79 |
| Found (C, H) % | 66.02, 7.57 | 65.26, 6.73 | 66.41, 5.71 |
| High resolution power mass spectrum |  |  |  |
| Calc. (m/Z) | — | — | — |
| Found (m/Z) | — | — | — |

EXAMPLE 8

Synthesis of 15β-hydroxyailanthone-2-methyl saturated fatty acid esters (i.e., the compound (1)) according to the present invention A 1.0 mM amount of 15β-hydroxyailanthone triacetate-2-methyl saturated fatty acid ester obtained in Example 4 was dissolved in a methanol solution containing a 0.85 equivalent of potassium methoxide and a 0.85 equivalent of 18-crown-6. The mixture was allowed to stand at room temperature for 4 hours under a nitrogen atmosphere while stirring.

The reaction mixture thus obtained was treated in the same manner as in Example 7. Thus, the desired compounds in the form of colorless amorphous powder were obtained.

The structures and the physico-chemical data of the compound Nos. 92 to 94 thus obtained are shown in Table 7.

EXAMPLE 9

Synthesis of 15β-hydroxyailanthone-2-hydroxycarboxylic acid esters (i.e., the compound (1)) according to the present invention A 100 mg amount of 15β-hydroxyailanthone-2-methoxymethloxy carboxylic acid ester was dissolved in 10 ml of a solution prepared by dissolving 52.6 g of hydrogen chloride in 100 ml of methanol. The solution was allowed to stand at a room temperature for 20 minutes while stirring. The solvent was distilled off in vacuo and the residue thus obtained was dissolved in methylene chloride. The methylene chloride phase was washed with water (twice) and then with a saturated aqueous sodium chloride solution (three times) and, then, was dried over anhydrous magnesium sulfate. The methylene chloride was distilled off. Thus, the desired compounds in the form of colorless amorphous powder were obtained.

The structures and the physico-chemical data of the compound Nos. 95 and 96 are shown in Table 8.

TABLE 7

| | Compound No. | | |
|---|---|---|---|
| | 92 | 93 | 94 |
| R | O‖ –C–⋀⋀⋀⋀ | O‖ –C–⋀⋀⋀⋀ | O‖ –C–⋀⋀⋀⋀ |
| | (2'-R, 2'-S mixture) | (2'-R, 2'-S mixture) | (2'-R, 2'-S mixture) |
| Specific rotatory power $[\alpha]_D^{25-30°\,C.}$ (CHCl$_3$) | +52.9° (C = 0.28) | +41.4° (C = 0.23) | +35.5° (C = 0.31) |
| Infrared absorption (KBr, cm$^{-1}$) | 3480, 1750, 1675, 1625 | 3480, 1750, 1675, 1630 | 3450, 1750, 1670, 1620 |
| Ultraviolet absorption ($\lambda_{max}^{EtOH}$, nm) | 238 (ε9200) | 238 (ε9700) | 238 (ε11000) |
| Mass spectrum (m/Z) | 532 (M$^+$), 444, 374, 344 | 560 (M$^+$), 488, 430, 374, 330 | 616 (M$^+$), 544, 448, 330 |
| Proton NMR | One isomer 92a | One isomer 93a | One isomer 94a |
| (100 MHz, CDCl$_3$) | 0.86 (3H, t) | 0.86 (3H, t, 10'-H$_3$) | 0.86 (3H, t, H$_3$) |
| δ in ppm, | 1.18 (3H, s) | 1.20–1.80 (14H, m, | 1.20–1.80 (22H, m, |
| CHCl$_3$ chemical shift (δ7.24) | 1.18 (3H, d, J=8Hz) | 3'-9'-H$_2$) | 3'-13'-H$_2$) |
| was used as internal standard) | 1.24–1.80 (10H, m) | The other signals exhibited | The other signals exhibited the same |
| | 2.01 (3H, s), 2.32 (1H, m) | the same shift values as | shift values as in compound No. 92a |
| | 2.48 (1H, m), 2.84 (1H, d, J12H) | in compound No. 92a | |
| | 2.96 (1H, m), 3.02 (1H, s) | | |
| | 3.52, 3.90 (each 1H, d, J=8Hz) | | |
| | 4.03 (1H, s), 4.15 (1H, s) | | |
| | 4.58 (1H, t), 5.17, 5.36 (each | | |
| | 1H, s), 5.64 (1H, d, J=12Hz) | | |
| | 6.14 (1H, brs) | | |
| | The other isomer 92b | The other isomer 93b | The other isomer 94b |
| | 1.16 (3H, d, J=8Hz, 2'-CH$_3$) | 0.86 (3H, t, 10'-H$_3$) | 0.86 (3H, t, 14'-H$_3$) |
| | The other signals exhibited | 1.20–1.80 (14H.m, | 1.20–1.80 (22H, m, |
| | the same shift values | 3'-9-H$_2$) | 3'-13'-H$_2$) |
| | as in compound 92a. | The other signals exhibited | The other signals exhibited the same |
| | | the same shift values as | shift values as in compound No. 92b |
| | | in compound No. 92b | |
| Molecular formula | C$_{29}$H$_{40}$O$_9$ | C$_{31}$H$_{44}$O$_9$ | C$_{35}$H$_{52}$O$_9$ |
| Elemental analysis | | | |
| Calc. (C, H)% | 65.39, 7.57 | — | 68.15, 8.50 |
| Found (C, H)% | 65.43, 7.71 | | 67.93, 8.38 |
| High resolution power mass spectrum | | | |
| Calc. (m/Z) | — | 560.2982 | — |
| Found (m/Z) | | 560.2972 | |

TABLE 8

| | Compound No. | |
|---|---|---|
| | 95 | 96 |
| R | $\overset{O}{\underset{\|}{-C}}-\overset{OH}{\underset{\|}{CH}}(CH_2)_6CH_3$ | $\overset{O}{\underset{\|}{-C}}-\overset{OH}{\underset{\|}{CH}}(CH_2)_{11}CH_3$ |
| | (2'-R, + 2'-S mixture) | (2'-R + 2'-S mixture) |
| Specific rotatory power $[\alpha]_D^{26}$ (CHCl$_3$) | +35.3° (C = 0.36) | +36.4° (C = 0.11) |
| Infrared absorption (KBr, cm$^{-1}$) | 3300, 1760, 1680, 1620 | 3300, 1750, 1660, 1620 |
| Ultraviolet absorption ($\lambda_{max}^{EtOH}$, nm) | 238 ($\epsilon$9880) | 238 ($\epsilon$10100) |
| Mass spectrum (m/Z) | 548 (M$^+$), 530, 504, 486 | 618 (M$^+$), 600, 574, 556, 530 |
| Proton NMR | One isomer | One isomer |
| (100 MHz, COCl$_3$, δ in ppm, CHCl$_3$ chemical shift (δ7.24) was used as internal standard) | 0.85 (3H, t) | 0.85 (3H, t) |
| | 1.17 (3H, s) | 1.26 (20H, s) |
| | 1.26 (10H, s) | 1.60 (2H, brs) |
| | 2.00 (3H, s) | 4.24 (1H, t, J=6Hz) |
| | 2.28 (2H, m) | The other isomer |
| | 3.03 (1H, s) | 4.28 (1H, t, J=6Hz, 2'-H) |
| | 3.54, 3.90 (each 1H, d, J=8Hz) | The other signals exhibited the same shift values as in compound No. 95 |
| | 4.03 (1H, s) | |
| | 4.17 (1H, s,) | |
| | 4.24 (1H, t, J=6Hz) | |
| | 4.58 (1H, t) | |
| | 5.20, 5.37 (each 1H, s) | |
| | 5.78 (1H, d, J=12Hz) | |
| | 6.14 (1H, brs) | |
| | The other isomer | |
| | 4,28 (1H, t, J=6Hz 2'-H) | |
| Molecular formula | C$_{29}$H$_{40}$O$_{10}$ | C$_{34}$H$_{50}$O$_{10}$ |
| Elemental analysis | | |
| Calc. (C, H)% | — | 66.00, 8.15 |
| Found (C, H)% | | 65.87, 8.09 |
| High resolution power mass spectrum | | |
| Calc. (m/Z) | 548.2619 | — |
| Found (m/Z) | 548.2594 | |

EXAMPLE 10

Synthesis of 15β-hydroxyailanthone-2-aminocarboxylic acid esters (i.e., the compound (1)) according to the present invention A 100 mg amount of 15β-hydroxyailanthone-2-(N-t-butoxycarbonyl) amino carboxylic acid ester was dissolved in 10 ml of a solution prepared by dissolving 4.8 g of hydrochloric acid in 100 ml of ethyl acetate. The solution was allowed to stand at room temperature for 2 hours while stirring.

The solvent was distilled off in vacuo and the resultant residue was washed with n-hexane. Thus, the desired compounds in the form of colorless amorphous powder were obtained.

The structures and the physico-chemical data of the compound Nos. 97 to 99 are shown in Table 9.

TABLE 9

| | Compound No. | | |
|---|---|---|---|
| | 97 | 98 | 99 |
| R | $\overset{O}{\underset{\|}{-C}}-\overset{NH_3Cl}{\underset{\|}{CH}}(CH_2)_5CH_3$ | $\overset{O}{\underset{\|}{-C}}-\overset{NH_3Cl}{\underset{\|}{CH}}(CH_2)_5CH_3$ | $\overset{O}{\underset{\|}{-C}}-\overset{NH_3Cl}{\underset{\|}{CH}}CH_2CH(CH_3)_2$ |
| | (2'-S) | (2'-R) | (2'-S, L-Leucine) |
| Specific rotatory power $[\alpha]_D^{26}$ (EtOH) | +72.3° (C = 0.13) | +60.0° (C = 0.12) | +56.0° (C = 0.15) |
| Infrared absorption (KBr, cm$^{-1}$) | 3400, 1750, 1660, 1620 | 3400, 1750, 1680 1630 | 3400, 1750, 1670 1620 |
| Ultraviolet absorption ($\lambda_{max}^{EtOH}$, nm) | 238 ($\epsilon$8000) | 239 ($\epsilon$7670) | 238 ($\epsilon$9120) |
| Mass spectrum (m/Z) | 515, 487 (M$^+$: Not observed) | | 505 (M$^+$-HCl), 487, 461, 443 |
| Proton NMR | 0.77 (3H, t) | 0.76 (3H, t) | 1.11 (6H, d, J=5Hz) |
| (100 MHz, D$_2$O, δ in ppm, TSP chemical shift (δ0.00) was used as internal standard) | 1.07 (3H, s) | 1.07 (3H, s) | 1.28 (3H, s) |
| | 1.22 (8H, s) | 1.20 (8H, s) | 1.80-2.00 (3H, m) |
| | 1.93 (3H, s) | 1.93 (3H, s) | 2.15 (3H, s) |
| | 2.97 (1H, s) | 2.96 (1H, s) | 3.17 (1H, s) |
| | 3.18 (1H, d, J=12Hz) | 3.02 (1H, d, J=12Hz) | 3.38 (1H, d, J=12Hz) |
| | 3.54 (1H, d, J=8Hz) | 3.46 (1H, d, J=8Hz) | 3.75 (1H, d, J=8Hz) |
| | 4.78 (1H, t) | 5.25, 5.33 (each 1H, s) | 5.00 (1H, t) |
| | 5.26, 5.37 (each 1H, s) | 5.83 (1H, d, J=12Hz) | 5.48, 5.58 (each 1H, s) |
| | 5.86 (1H, d, J=12Hz) | 6.04 (1H, brs) | 6.07 (1H, d, J=12Hz) |
| | 6.04 (1H, brs) | | 6.26 (1H, brs) |

EXAMPLE 11

Evaluation of Antineoplastic Activity of the Compounds according to the Present Invention The antineoplastic activity of the compound Nos. 46 to 48, 52 to 61, 67 to 72, 74 to 79 and 83 to 99 according to the present invention was evaluated as follows. $10^6$ cells of mouse lymphocytic leukemia P 388 were intraperitoneally injected into mice (i.e., BDF "1", females, 4–5 weeks age, average body weight of 18 g). The test was carried out by using 6 mice in each group.

The compounds listed in Table 10 below were successively administered in the doses listed in Table 10 for 5 days from the second day after the injection. The survival percentages (ILS) of the mice administered the compounds were calculated by the following equation:

$$ILS\,(\%) = \frac{\text{Average number of survival day of the administered group}}{\text{Average number of survival day of the control group}} \times 100 - 100$$

The results are shown in Table 10.

As is clear from the results shown in Table 10, the compounds (1) according to the present invention were remarkably effective against mouse lymphocytic leukemia P 388. Especially, the compound Nos. 53, 54, 55, 58, 68, 69, 79, and 93 prolonged the life of the administered group to twice that of the control group. Thus, it is believed that the present compounds are effective as an antitumor agent.

TABLE 10

| Compound No. | 50 | 40 | 30 | 20 | 10 | 5.0 | 2.5 | 1.0 | 0.5 | 0.25 | 0.10 | 0.05 |
|---|---|---|---|---|---|---|---|---|---|---|---|---|
| 46 | *2 |  | 57 |  | 39 | 20 |  |  |  |  |  |  |
| 47 |  | (Toxic) 16 | 47 |  | 45 | 45 | 24 |  |  |  |  |  |
| 48 |  | 29 | 24 |  | 17 | — | 0 |  |  |  |  |  |
| 52 |  | Toxic*3 | 54 | 36 | 41 | 32 | 20 |  |  |  |  |  |
| 53 |  |  |  |  | Toxic | Toxic | 74 | 42 | 33 |  | 28 |  |
| 54 |  |  |  |  | 97 | 70 | 67 | 28 | 30 |  | 14 |  |
| 55 |  | Toxic | Toxic | Toxic | (Toxic) 34 | 75 | 56 | 33 | 12 | 5 | 7 |  |
| 56 |  | Toxic | Toxic | Toxic | Toxic | 63 | 56 |  |  |  |  |  |
| 57 |  |  | Toxic | (Toxic) 53 | (Toxic) 46 | 49 | 41 |  |  |  |  |  |
| 58 |  | Toxic | (Toxic) 15 | (Toxic) 15 | 80 | 60 | 56 |  |  |  |  |  |
| 59 |  | Toxic | 59 | 58 | 36 | 51 | 24 |  |  |  |  |  |
| 60 |  | Toxic | 63 | 51 | 46 | 42 | 22 |  |  |  |  |  |
| 60' |  | (Toxic) 10 | (Toxic) 44 | 58 | 49 | 20 | 17 |  |  |  |  |  |
| 61 |  | 17 | 15 | 17 | 14 | 7 | — |  |  |  |  |  |
| 67 |  | Toxic | Toxic | Toxic | Toxic | Toxic | Toxic | Toxic | Toxic | 46 | 32 |  |
| 68 |  |  |  |  | Toxic | 73 | 53 | 42 | 23 |  | 23 |  |
| 69 |  |  |  |  | (Toxic) 27 | 75 | 58 | 35 | 25 |  | 18 |  |
| 70 |  |  |  |  | (Toxic) 57 | 62 | 47 | 27 | 20 |  | 8 |  |
| 71 |  |  |  |  | Toxic | 49 | 25 | 17 | 9 |  | 5 |  |
| 72 |  |  |  |  | 53 | 32 | 19 | 9 | 10 |  | 12 |  |
| 74 | Toxic | 47 | 35 | 26 | 17 | 22 | 16 |  |  |  |  |  |
| 75 |  | 45 | 38 | 38 | 16 | 12 | 12 |  |  |  |  |  |
| 76 |  |  |  |  | Toxic | 17 | 12 | 12 | 10 |  |  |  |
| 77 |  |  |  | Toxic 31 | 61 | 39 | 31 | 15 | 12 |  |  |  |
| 78 |  |  |  |  | 58 | 31 | 22 | 9 | 5 | 3 |  |  |
| 79 |  | Toxic | 78 | 78 | 59 | 31 | 19 | 2 | 2 |  |  |  |
| 83 |  |  |  |  | Toxic | 61 | 46 | 42 | 33 |  |  |  |
| 84 |  |  |  |  |  | Toxic | 52 | 38 | 35 |  | 13 |  |
| 85 |  |  |  |  |  | Toxic | 42 | 53 |  |  | 32 | 17 |
| 86 |  |  |  |  |  | 68 | 67 | 50 | 45 |  | 23 |  |
| 87 |  |  |  |  |  | Toxic | 66 | 49 | 37 |  | 19 |  |
| 88 |  |  |  |  | (Toxic) 45 | 63 | 52 | 43 | 38 |  | 23 |  |
| 89 |  |  |  |  | (Toxic) 25 | 48 | 25 | 22 | 17 |  | 5 |  |
| 90 |  |  |  |  |  | Toxic | 58 | 53 |  |  |  |  |
| 91 |  |  |  | 57 | 52 | 40 |  |  |  |  |  |  |
| 92 |  | Toxic | 67 | 42 | 45 | 27 | 23 |  |  |  |  |  |
| 93 |  | Toxic | 80 | 70 | 48 | 37 | 28 |  |  |  |  |  |
| 94 |  |  | Toxic | 58 | 65 | 28 | 27 |  |  |  |  |  |
| 95 |  |  | Toxic | (Toxic) 28 | 43 | 38 | 33 |  |  |  |  |  |
| 96 |  |  | Toxic | Toxic | 33 | 41 | 29 |  |  |  |  |  |
| 97 |  |  | 42 |  | 47 | 24 |  |  |  |  |  |  |
| 98 |  |  | Toxic |  | 64 | 51 |  |  |  |  |  |  |
| 99 |  | (Toxic) 17 | (Toxic) 17 | (Toxic) 20 | 32 | 29 | 25 |  |  |  |  |  |

TABLE 10-continued

| Compound | Dose (mg/kg) | | | | | | | | | | |
|---|---|---|---|---|---|---|---|---|---|---|---|
| No. | 50 | 40 | 30 | 20 | 10 | 5.0 | 2.5 | 1.0 | 0.5 | 0.25 | 0.10 | 0.05 |
| Mitomycin C[*1] | | | | | | | | 83 | | | | |

[*1]Antitumor agent manufactured by Kyowa Hakko Kogyo Co., Ltd.
[*2]All blanks in the Table means that no test was carried out.
[*3]Toxic means that mice died during administration.

What is claimed is:

1. An ailanthone derivative having the formula:

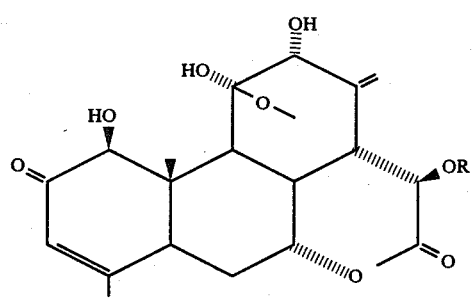
(I)

wherein R is a 3,4-dimethyl-4-acyloxy-2-pentenoic acid residue having 9 to 15 carbon atoms.

2. An ailanthone derivative having the formula:

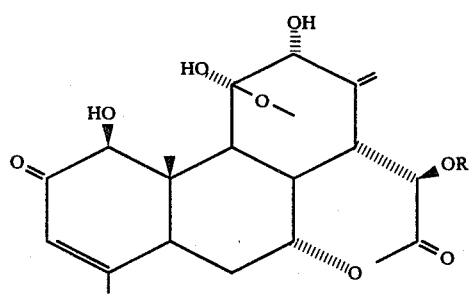
(I)

wherein R is a 3,4,4-trimethyl-2-pentenoic acid residue having the formula:

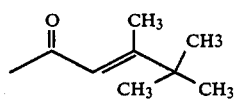

3. An ailanthone derivative having the formula:

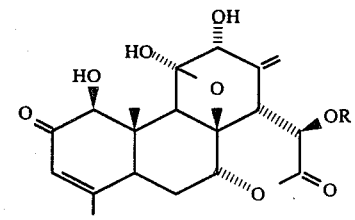
(I)

wherein R is a 3,4-dimethyl-4-acyloxy-2-pentenoic acid residue having 9 to 15 carbon atoms.

4. An ailanthone derivative having the formula:

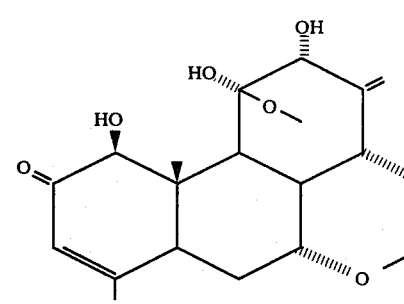
(I)

wherein R is a residue having the formula:

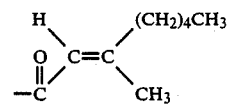

5. An ailanthone derivative having the formula:

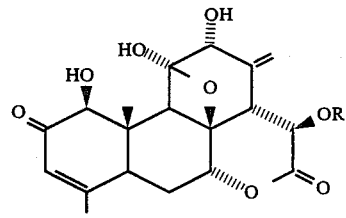
(I)

wherein R is

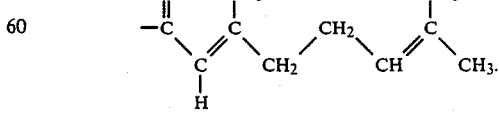

* * * * *